(12) United States Patent
Buesing et al.

(10) Patent No.: US 9,034,485 B2
(45) Date of Patent: *May 19, 2015

(54) COMPOUNDS FOR ELECTRONIC DEVICES

(75) Inventors: Arne Buesing, Frankfurt am Main (DE); Holger Heil, Frankfurt am Main (DE); Philipp Stoessel, Frankfurt am Main (DE); Amir Hossain Parham, Frankfurt am Main (DE); Rocco Fortte, Frankfurt am Main (DE); Jonas Valentin Kroeber, Frankfurt am Main (DE)

(73) Assignee: Merck Patent GmbH, Darmststdt (DE)

( * ) Notice: Subject to any disclaimer, the term of this patent is extended or adjusted under 35 U.S.C. 154(b) by 294 days.

This patent is subject to a terminal disclaimer.

(21) Appl. No.: 13/143,976

(22) PCT Filed: Dec. 22, 2009

(86) PCT No.: PCT/EP2009/009219
§ 371 (c)(1),
(2), (4) Date: Jul. 11, 2011

(87) PCT Pub. No.: WO2010/083871
PCT Pub. Date: Jul. 29, 2010

(65) Prior Publication Data
US 2011/0266533 A1    Nov. 3, 2011

(30) Foreign Application Priority Data
Jan. 20, 2009    (DE) .......................... 10 2009 005 290

(51) Int. Cl.
| | | |
|---|---|---|
| H01L 51/54 | (2006.01) |
| H01L 51/00 | (2006.01) |
| C07D 219/02 | (2006.01) |
| C07D 265/38 | (2006.01) |
| C07D 279/36 | (2006.01) |
| C07D 401/04 | (2006.01) |
| C07D 471/04 | (2006.01) |
| C07D 495/04 | (2006.01) |
| C09B 5/60 | (2006.01) |
| C09B 57/00 | (2006.01) |
| C09B 3/14 | (2006.01) |
| C09B 3/78 | (2006.01) |
| C09B 5/24 | (2006.01) |
| H01L 51/50 | (2006.01) |

(52) U.S. Cl.
CPC .......... *H01L 51/0072* (2013.01); *C07D 219/02* (2013.01); *C07D 265/38* (2013.01); *C07D 279/36* (2013.01); *C07D 401/04* (2013.01); *C07D 471/04* (2013.01); *C07D 495/04* (2013.01); *H01L 51/0059* (2013.01); *H01L 51/006* (2013.01); *H01L 51/5012* (2013.01); *H01L 51/5048* (2013.01); *C09B 5/60* (2013.01); *C09B 57/00* (2013.01); *C09B 57/001* (2013.01); *C09B 57/008* (2013.01); *C09B 3/14* (2013.01); *C09B 3/78* (2013.01); *C09B 5/24* (2013.01); *Y02E 10/549* (2013.01); *Y10S 428/917* (2013.01)

(58) Field of Classification Search
USPC .................. 428/690, 917; 313/504, 505, 506; 257/40, E51.05, E51.026, E51.032; 548/304.4, 418, 440; 546/47, 81, 101; 544/179, 183, 233, 245, 342
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,811,834 A * | 9/1998 | Tamano et al. ................. | 257/40 |
| 5,840,217 A | 11/1998 | Lupo et al. | |
| 6,458,909 B1 | 10/2002 | Spreitzer et al. | |
| 6,908,783 B1 | 6/2005 | Kuehl et al. | |
| 7,858,967 B2 | 12/2010 | Pfeiffer et al. | |
| 2005/0040390 A1 | 2/2005 | Pfeiffer et al. | |
| 2005/0121667 A1 | 6/2005 | Kuehl et al. | |
| 2005/0258742 A1 | 11/2005 | Tsai et al. | |
| 2006/0063027 A1 | 3/2006 | Vestweber et al. | |
| 2006/0166038 A1 | 7/2006 | Park et al. | |
| 2006/0175958 A1 | 8/2006 | Gerhard et al. | |
| 2007/0170419 A1 | 7/2007 | Gerhard et al. | |
| 2007/0176541 A1 * | 8/2007 | Son et al. ...................... | 313/504 |
| 2008/0220285 A1 | 9/2008 | Vestweber et al. | |
| 2009/0066225 A1 | 3/2009 | Kimura et al. | |
| 2009/0072712 A1 | 3/2009 | Stoessel et al. | |
| 2009/0134384 A1 | 5/2009 | Stoessel et al. | |
| 2009/0295275 A1 * | 12/2009 | Parham et al. ................. | 313/504 |
| 2009/0302752 A1 | 12/2009 | Parham et al. | |
| 2010/0187505 A1 | 7/2010 | Stoessel et al. | |
| 2010/0227978 A1 | 9/2010 | Stoessel et al. | |
| 2010/0331506 A1 | 12/2010 | Fortte et al. | |
| 2011/0049501 A1 | 3/2011 | Bold et al. | |

FOREIGN PATENT DOCUMENTS

| | | |
|---|---|---|
| DE | 102005043163 A1 | 3/2007 |
| EP | 0 676 461 A2 | 10/1995 |
| EP | 1 191 612 A2 | 3/2002 |
| EP | 1 191 613 A2 | 3/2002 |
| EP | 1 191 614 A2 | 3/2002 |
| EP | 1476881 A2 | 11/2004 |
| EP | 1596445 A1 | 11/2005 |
| JP | 2006-199698 A | 8/2006 |
| JP | 2007-142308 A | 6/2007 |
| JP | 2007-211010 A | 8/2007 |
| JP | 2008-090297 A | 4/2008 |

(Continued)

*Primary Examiner* — Gregory Clark
(74) *Attorney, Agent, or Firm* — Drinker Biddle & Reath LLP

(57) ABSTRACT

The present invention relates to compounds of the formula (1) and to the use thereof in organic electronic devices, and to organic electronic devices which comprise compounds of the formula (1), preferably as hole-transport materials and/or as emitting materials.

13 Claims, 1 Drawing Sheet

(56) References Cited

FOREIGN PATENT DOCUMENTS

| | | |
|---|---|---|
| TW | 200902498 A | 1/2009 |
| WO | WO-98/27136 A1 | 6/1998 |
| WO | WO-00/70655 A2 | 11/2000 |
| WO | WO-01/41512 A1 | 6/2001 |
| WO | WO-02/02714 A2 | 1/2002 |
| WO | WO-02/15645 A1 | 2/2002 |
| WO | WO-03/070822 A2 | 8/2003 |
| WO | WO-2004/058911 A2 | 7/2004 |
| WO | WO-2004/081017 A1 | 9/2004 |
| WO | WO-2005/011013 A1 | 2/2005 |
| WO | WO-2005/019373 A2 | 3/2005 |
| WO | WO-2005/033244 A1 | 4/2005 |
| WO | WO-2005/084081 A1 | 9/2005 |
| WO | WO-2005/084082 A1 | 9/2005 |
| WO | WO 2006/033563 * | 3/2006 ............ C09K 11/06 |
| WO | WO-2006/048268 A1 | 5/2006 |
| WO | WO-2006/100896 A1 | 9/2006 |
| WO | WO-2006/117052 A1 | 11/2006 |
| WO | WO-2006/122630 A1 | 11/2006 |
| WO | WO-2007031165 A2 | 3/2007 |
| WO | WO-2007/064104 A1 | 6/2007 |
| WO | WO-2007064104 A1 | 6/2007 |
| WO | WO-2008/145239 A2 | 12/2008 |
| WO | WO 2010/050778 A1 | 5/2010 |
| WO | WO 2010/064871 A1 | 6/2010 |

* cited by examiner

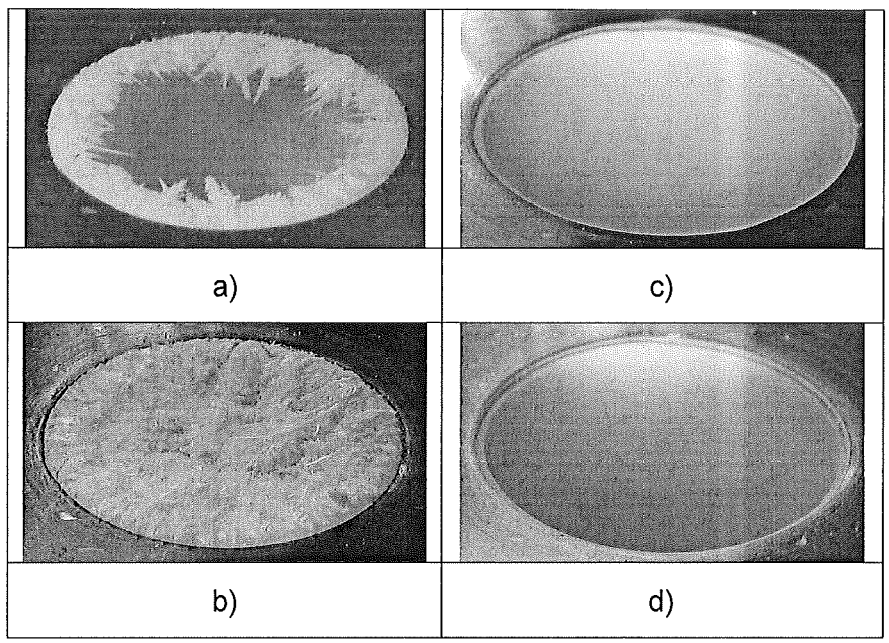
a) HTM1, after vapour deposition for 1 h
b) HTM1, after vapour deposition for 2 h
c) Example Compound 3, after vapour deposition for 1 h
d) Example Compound 3, after vapour deposition for 2 h

COMPOUNDS FOR ELECTRONIC DEVICES

CROSS-REFERENCE TO RELATED APPLICATIONS

This application is a national stage application (under 35 U.S.C. §371) of PCT/EP2009/009219, filed Dec. 22, 2009, which claims benefit of German application 10 2009 005 290.9, filed Jan. 20, 2009.

BACKGROUND OF THE INVENTION

The present invention relates to compounds of the formula (1) and to the use thereof in electronic devices, and to electronic devices which comprise these compounds.

The general structure of organic electroluminescent devices is described, for example, in U.S. Pat. Nos. 4,539,507, 5,151,629, EP 0676461 and WO 98/27136. However, there is still a need for improvement in these devices:
1. The efficiency should still be improved, especially in the case of fluorescent OLEDs.
2. The operating lifetime is still short, in particular in the case of blue emission, and consequently there is still a need for improvement here.
3. The operating voltage is quite high, especially in the case of fluorescent OLEDs, and should therefore be reduced further in order to improve the power efficiency. This is of major importance, in particular, for mobile applications. Further improvements are desirable here, in particular in the case of charge-transport materials.
4. In the case of hole-transport materials in accordance with the prior art, the voltage is dependent on the layer thickness of the hole-transport layer. In practice, a greater layer thickness of the hole-transport layer would frequently be desirable. However, this cannot be achieved using materials in accordance with the prior art owing to the associated increase in voltage.
5. Many materials which are used in accordance with the prior art in organic electroluminescent devices tend to crystallise on the vapour-deposition source in the process for the production of the electroluminescent device and thus clog the vapour-deposition source. These materials can therefore only be employed in mass production with increased technical complexity.

Arylamines are used as hole-transport and -injection materials. Materials of this type based on indenofluorenes are disclosed, for example, in WO 06/100896 and WO 06/122630. The indenofluorenamines described above have disadvantages in processability: during the vapour-deposition or coating process, premature deposition and thus a complication of the industrial process may occur. In addition, hole-transporting materials generally frequently have low electron stability, which results in short lifetimes of the associated diodes in operation. There continues to be a need for improvement here.

Furthermore, quinacridine derivatives and the use thereof in electronic devices are disclosed in WO 07/064,104.

BRIEF SUMMARY OF THE INVENTION

The present invention describes piperidine derivatives and related heterocyclic derivatives as a new class of materials having emitting and hole-transporting properties, in particular for use in the emission and/or hole-transport and/or hole-injection layer of electroluminescent devices.

Surprisingly, the use of the compounds according to the invention gives rise to improvements compared with the prior art. The reduction in the operating voltage at the same time as increased hole mobility and the improvement in the lifetime, possibly owing to increased electron stability, achieved through raising of the energy level of the LUMO, are to the forefront here. In addition, this class, through its flexible geometry, exhibits a lower tendency towards crystallisation than arylamines in accordance with the prior art.

It has furthermore been found that the compounds according to the invention are very highly suitable for use in organic electroluminescent devices comprising phosphorescent emitters. Particularly favourable results with respect to lifetime and energy efficiency of the electroluminescent devices are obtained on use of the compounds of the formula (1) in the hole-transport layer or emitting layer of devices comprising phosphorescent emitters. The invention thus relates to a compound of the formula (1)

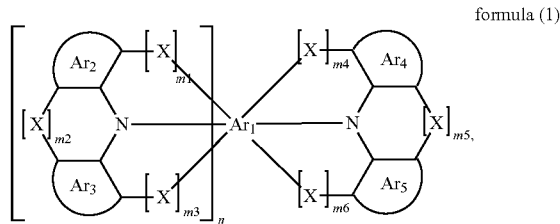

formula (1)

where the following applies to the symbols and indices used:

$X$ is on each occurrence, identically or differently, a divalent bridge selected from the group consisting of $B(R^1)$, $C(R^1)_2$, $Si(R^1)_2$, $C=O$, $C=NR^1$, $C=C(R^1)_2$, $O$, $S$, $S=O$, $SO_2$, $N(R^1)$, $P(R^1)$ and $P(=O)R^1$;

$Ar_1$ is an aromatic ring system having 10 to 40 aromatic ring atoms or a heteroaromatic ring system having 5 to 40 aromatic ring atoms, each of which may be substituted by one or more radicals $R^1$;

$Ar_2$ to $Ar_5$ are, identically or differently on each occurrence, an aromatic or heteroaromatic ring system having 5 to 40 aromatic ring atoms, which may in each case be substituted by one or more radicals $R^1$;

$R^1$ is on each occurrence, identically or differently, selected from the group consisting of H, D, F, Cl, Br, I, CHO, $N(R^2)_2$, $N(Ar_6)_2$, $C(=O)Ar_6$, $P(=O)(Ar_6)_2$, $S(=O)Ar_6$, $S(=O)_2Ar_6$, $CR^2=CR^2Ar_6$, CN, $NO_2$, $Si(R^2)_3$, $B(OR^2)_2$, $OSO_2R^2$, a straight-chain alkyl, alkenyl, alkoxy and thioalkoxy group having 1 to 40 C atoms and a branched, mono- or polycyclic alkyl, alkenyl, alkoxy and thioalkoxy group having 3 to 40 C atoms, each of which may be substituted by one or more radicals $R^2$, where one or more non-adjacent $CH_2$ groups may be replaced by $R^2C=CR^2$, $C=C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by F, Cl, Br, I, CN or $NO_2$, and an aromatic or heteroaromatic ring system having 5 to 40 aromatic ring atoms, which may in each case be substituted by one or more radicals $R^2$, and an aryloxy or heteroaryloxy group having 5 to 40 aromatic ring atoms, which may be substituted by one or more radicals $R^2$, and a combination of these systems, where two or more adjacent substituents $R^1$ may also form a mono- or polycyclic, aliphatic or aromatic ring system with one another;

$R^2$ is on each occurrence, identically or differently, selected from the group consisting of H, D, F, Cl, Br, I, CHO, $N(R^3)_2$, $N(Ar_6)_2$, $C(=O)Ar_6$, $P(=O)(Ar_6)_2$, $S(=O)Ar_6$, $S(=O)_2Ar_6$, $CR^3=CR^3Ar_6$, CN, $NO_2$, $Si(R^3)_3$, $B(OR^3)_2$, OSO$_2$R$^3$, a straight-chain alkyl, alkoxy and thioalkoxy group having 1 to 40 C atoms and a branched, mono- or polycyclic alkyl, alkoxy and thioalkoxy group having 3 to 40 C atoms, each of which may be substituted by one or more radicals R$^3$, where one or more non-adjacent CH$_2$ groups may be replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O) (R$^3$), SO, SO$_2$, NR$^3$, O, S or CONR$^3$ and where one or more H atoms may be replaced by F, Cl, Br, I, CN or NO$_2$, and a combination of these systems, where two or more adjacent substituents R$^2$ may also form a mono- or polycyclic, aliphatic or aromatic ring system with one another;

R$^3$ is on each occurrence, identically or differently, H, F or an aliphatic, aromatic and/or heteroaromatic hydrocarbon radical having 1 to 20 C atoms, in which, in addition, one or more H atoms may be replaced by F atoms, where two or more adjacent substituents R$^3$ may also form a mono- or polycyclic, aliphatic or aromatic ring system with one another;

Ar$_6$ is on each occurrence, identically or differently, an aromatic or heteroaromatic ring system having 5 to 30 aromatic ring atoms, which may be substituted by one or more radicals R$^3$, where, in addition, two radicals Ar$_6$ which are bonded to the same nitrogen or phosphorus atom may be linked to one another by a single bond or a bridge selected from the group consisting of B(R$^3$), C(R$^3$)$_2$, Si(R$^3$)$_2$, C=O, C=NR$^3$, C=C(R$^3$)$_2$, O, S, S=O, SO$_2$, N(R$^3$), P(R$^3$) and P(=O)R$^3$;

m1 to m6 are on each occurrence, identically or differently, 0 or 1, where m=0 means that a hydrogen atom or radical R$^1$ is present instead of X, and where at least one of the indices m1, m3, m4 and/or m6=1; and n is 1, 2 or 3.

A BRIEF DESCRIPTION OF THE FIGURE

FIG. 1*a* illustrates the pictures of the upper edge of the vapor-deposition sources after vapor deposition at a rate of 0.1 nm/s after 1 hour.

FIG. 1*b* illustrates the pictures of the upper edge of the vapor-deposition sources after vapor deposition at a rate of 0.1 nm/s after 2 hours.

FIG. 1*c* illustrates the pictures of example compound 3 after vapor deposition for 1 hour.

FIG. 1*d* illustrates the pictures of example compound 3 after vapor deposition for 2 hours.

A DETAILED DESCRIPTION OF THE INVENTION

For the purposes of this invention, adjacent substituents are taken to mean substituents which are either bonded to the same atom, i.e., for example, the two substituents R$^1$ in a C(R$^1$)$_2$ group, or substituents which are bonded to directly adjacent atoms, i.e., for example, the two substituents R$^1$ in a C(R$^1$)—C(R$^1$) group.

For the purposes of this invention, an aryl group or heteroaryl group is taken to mean an aromatic group (aromatic hydrocarbon radical) or heteroaromatic group respectively having a common aromatic electron system, where an aryl group comprises 6 to 40, preferably 6 to 24 C atoms and a heteroaryl group comprises 2 to 40, preferably 2 to 24 C atoms and a total of at least 5 aromatic ring atoms. The heteroatoms are preferably selected from N, O and/or S. For the purposes of this invention, this may be a simple homocycle or heterocycle, for example benzene, pyridine, thiophene, etc., or it may be a condensed aromatic ring system in which at least two aromatic or heteroaromatic rings, for example benzene rings, are "fused" to one another, i.e. are condensed onto one another by anellation, i.e. have at least one common edge and thus also have a common aromatic system. The condensed aromatic rings here may be condensed in a linear or angular manner. The aryl or heteroaryl groups may be substituted or unsubstituted; any substituents present may likewise form further ring systems. Thus, for example, systems such as naphthalene, anthracene, phenanthrene, benzanthracene, pyrene, etc., are to be taken to be aryl groups and quinoline, acridine, benzothiophene, carbazole, etc., are to be taken to be heteroaryl groups for the purposes of this invention, while, for example, biphenyl, fluorene, spirobifluorene, etc., do not represent aryl groups since they involve separate aromatic electron systems. Aromatic ring systems which are anellated in a linear manner are, for example, anthracene, tetracene and pentacene. Aromatic ring systems which are anellated in an angular manner are, for example, phenanthrene, pyrene, chrysene and benzanthracene.

For the purposes of this invention, an aromatic ring system contains 6 to 40 C atoms in the ring system. For the purposes of this invention, a heteroaromatic ring system contains 2 to 40 C atoms and at least one hetero-atoamic in the ring system, with the proviso that the sum of the C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be connected by a short non-aromatic unit (less than 10% of the atoms other than H, preferably less than 5% of the atoms other than H), such as, for example, a C, N or O atom. Thus, for example, systems such as 9,9'-spirobifluorene, 9,9-diarylfluorene, triarylamine, diaryl ether, etc., are also intended to be taken to be aromatic ring systems for the purposes of this invention. Apart from the aryl and heteroaryl groups mentioned above, aromatic and heteroaromatic ring systems are, for the purposes of this invention, taken to mean, in particular, biphenylene, terphenylene, fluorene, spirobifluorene, dihydrophenanthrene, tetrahydropyrene and cis- or trans-indenofluorene.

For the purposes of the present invention, a C$_1$- to C$_{40}$-alkyl group, in which, in addition, individual H atoms or CH$_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, tert-pentyl, 2-pentyl, cyclopentyl, n-hexyl, s-hexyl, tert-hexyl, 2-hexyl, 3-hexyl, cyclohexyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2,2,2]octyl, 2-bicyclo[2,2,2]octyl, 2-(2,6-dimethyl)octyl, 3-(3,7-dimethyl)octyl, trifluoromethyl, pentafluoroethyl and 2,2,2-trifluoroethyl. For the purposes of this invention, an alkenyl group is particularly preferably taken to mean the radicals ethenyl, propenyl, butenyl, pentenyl, cyclopentenyl, hexenyl, cyclohexenyl, heptenyl, cycloheptenyl, octenyl and cyclooctenyl. For the purposes of this invention, an alkynyl group is particularly preferably taken to mean the radicals ethynyl, propynyl, butynyl, pentynyl, hexynyl, heptynyl and octynyl. A C$_1$- to C$_{40}$-alkoxy group is particularly preferably taken to mean methoxy, ethoxy, n-propoxy, i-propoxy, n-butoxy, i-butoxy, s-butoxy, t-butoxy and 2-methylbutoxy.

An aryl or heteroaryl group, which may be monovalent or divalent depending on the use, which may in each case be substituted by the above-mentioned radicals R$^1$ and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, $Ar_2$ to $Ar_5$ are, identically or differently on each occurrence, phenyl, 1-naphthyl or 2-naphthyl, particularly preferably phenyl or 2-naphthyl, very particularly preferably phenyl, each of which may be substituted by one or more radicals $R^1$.

Preference is thus given, in particular, to compounds of the following formula (2):

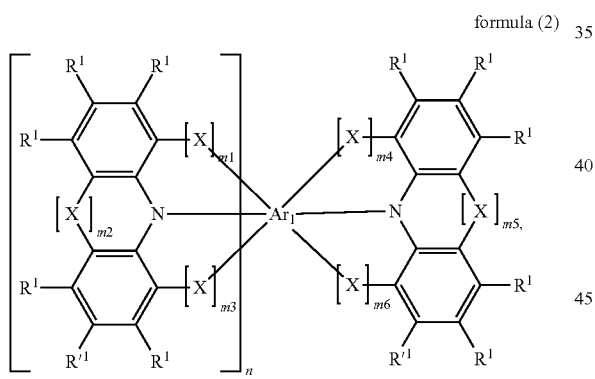

formula (2)

where the symbols and indices used have the meanings indicated above.

X in formula (1) or (2) furthermore preferably stands, identically or differently on each occurrence, for a divalent bridge $C(R^1)_2$, where $R^1$ is as defined above and is preferably on each occurrence, identically or differently, particularly preferably identically, selected from the group consisting of H, F, a straight-chain alkyl group having 1 to 6 C atoms, preferably methyl, where one or more H atoms may be replaced by F, and phenyl and naphthyl, preferably phenyl, each of which may be substituted by one or more radicals $R^2$, preferably methyl, but is particularly preferably unsubstituted, and a combination of these systems, where two or more adjacent substituents $R^1$ may also form a mono- or polycyclic, aliphatic or aromatic ring system with one another.

In a preferred embodiment of the invention, the group $Ar_1$ stands for a polycyclic aromatic ring system having 12 to 30 aromatic ring atoms or for a condensed aromatic hydrocarbon radical having 10 to 20 aromatic C atoms, each of which may be substituted by one or more radicals $R^1$.

In a particularly preferred embodiment of the invention, the group $Ar_1$ stands for a group of the following formulae (3) to (15):

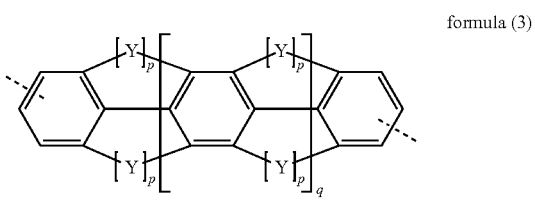

formula (3)

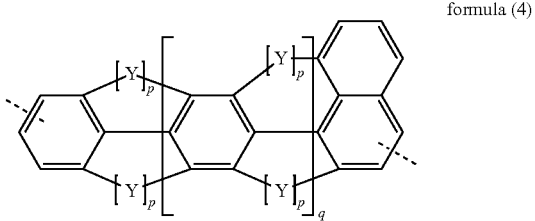

formula (4)

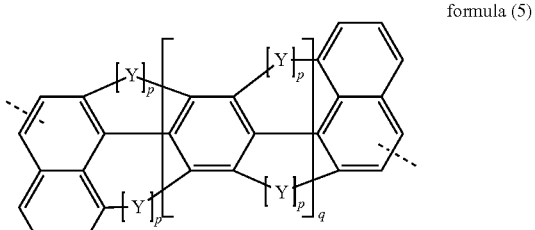

formula (5)

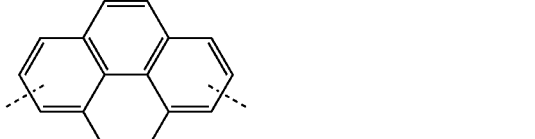

formula (6)

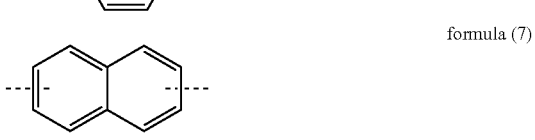

formula (7)

formula (8)

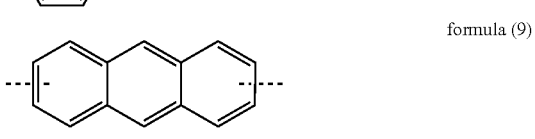

formula (9)

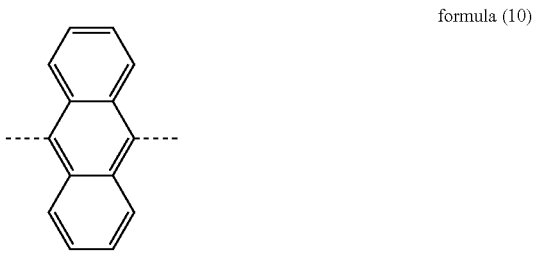

formula (10)

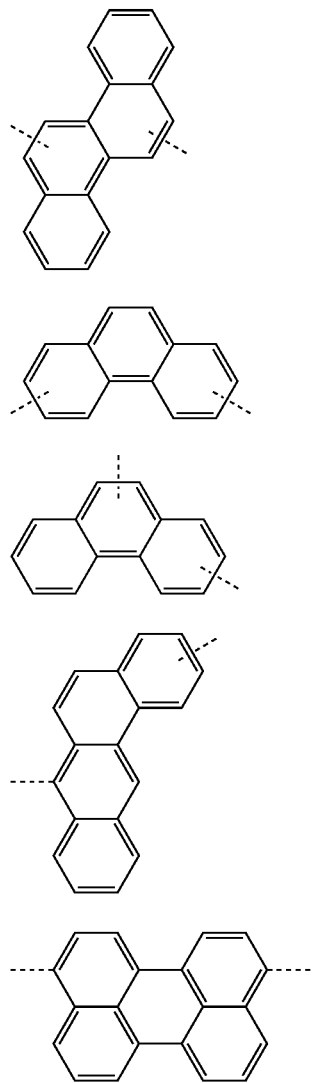

formula (11)

formula (12)

formula (13)

formula (14)

formula (15)

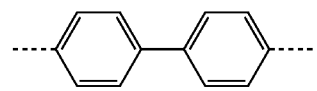

formula (16)

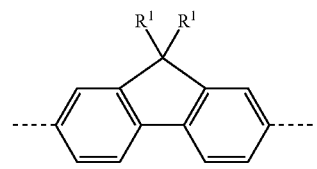

formula (17)

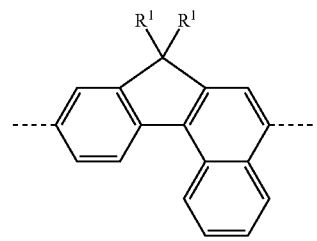

formula (18)

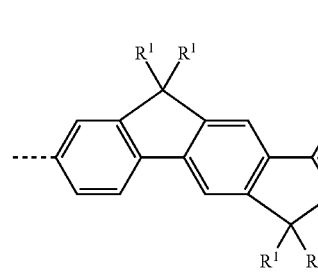

formula (19)

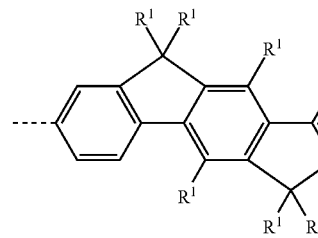

formula (20)

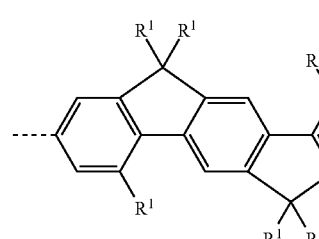

formula (21)

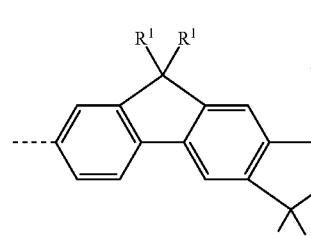

formula (22)

where these groups may each be substituted by one or more radicals $R^1$, where $R^1$ is as defined above, and in which furthermore:

Y has the same meaning as X and is preferably on each occurrence, identically or differently, a divalent bridge selected from the group consisting of $C(R^1)_2$, $Si(R^1)_2$, O, S, $N(R^1)$, $P(R^1)$, particularly preferably selected from the group consisting of $C(R^1)_2$, S and $N(R^1)$;

p is, identically or differently on each occurrence, 0 or 1, where, in the case of p=0, a hydrogen atom or radical $R^1$ is present instead of Y;

q is 0, 1 or 2, preferably 0 or 1; and the symbol "- - - -" stands for the respective single bond between a C atom of the group of the formulae (3) to (15) and one of the two nitrogen atoms shown in formula (1); if a group X is bonded to the unit $Ar_1$ this is preferably bonded at the position which is adjacent to the bond to the nitrogen.

A particularly preferred embodiment of the groups $Ar_1$ of the formulae (3) to (15) are the groups of the following formulae (16) to (48):

-continued
formula (23)
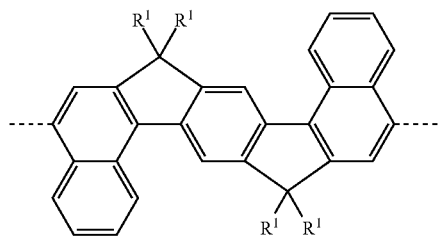
formula (24)
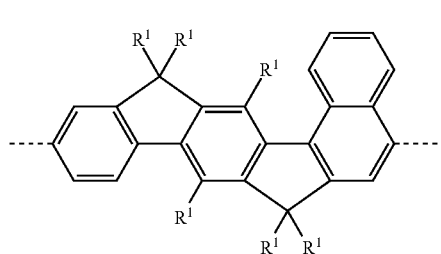
formula (25)
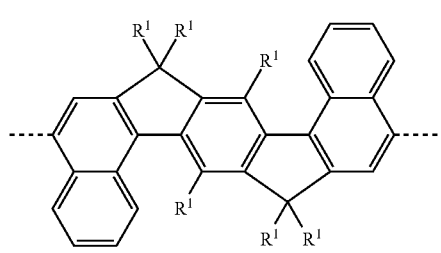
formula (26)
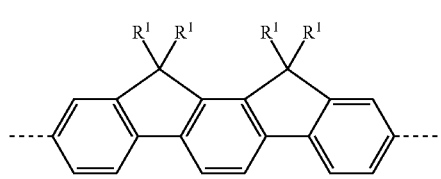
formula (27)
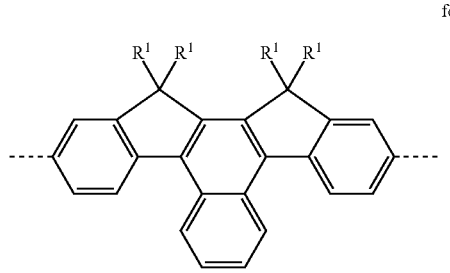
formula (28)
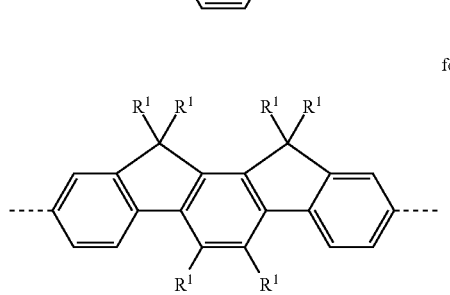
formula (29)
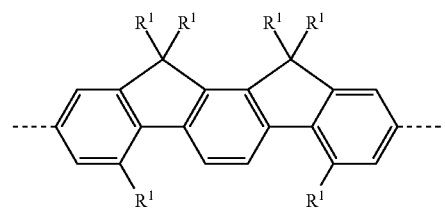
formula (30)
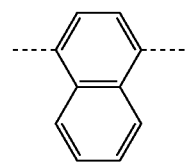
formula (31)
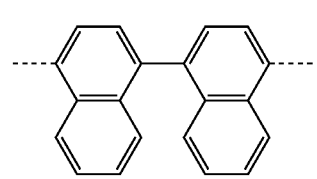
formula (32)
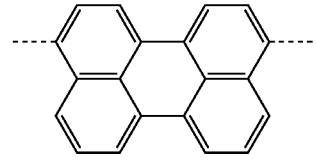
formula (33)
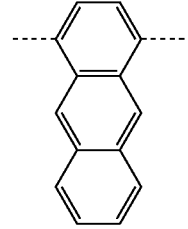
formula (34)
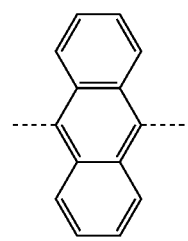
formula (35)
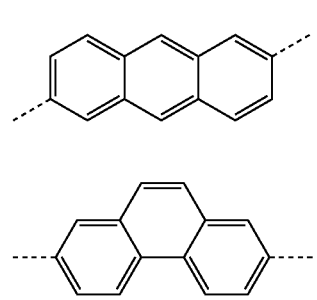
formula (36)

formula (37)–(48) [chemical structures]

where each of the above groups may furthermore in each case be substituted by one or more radicals R¹, but is preferably not further substituted;

where the symbol " ----- " in the above formulae stands for the respective single bond from $Ar_1$ to one of the two nitrogen atoms shown in formula 1; if a group X is bonded to the unit $Ar_1$, this is preferably bonded at the position which is adjacent to the bond to the nitrogen.

In a preferred embodiment of the invention, the radical R¹ in the structures of the formulae (41), (42), (43), (44) and (46) stands for phenyl, which may be substituted, identically or differently on each occurrence, by one or more alkyl groups having 1 to 4 C atoms.

If $Ar_1$ is selected from groups (16) to (48) depicted above, the index n=1.

In a further preferred embodiment of the invention, $Ar_1$ is a trivalent group selected from units of the formulae (49) to (51):

formula (49)

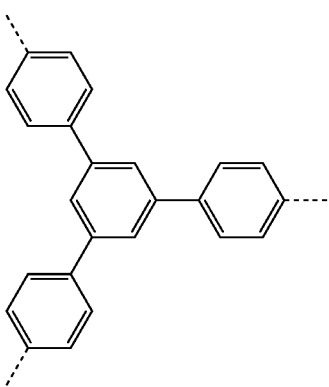

formula (50)

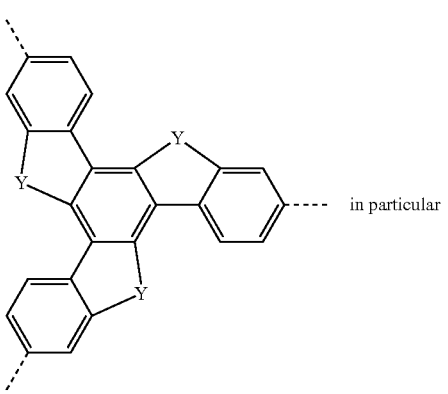

in particular formula (51)

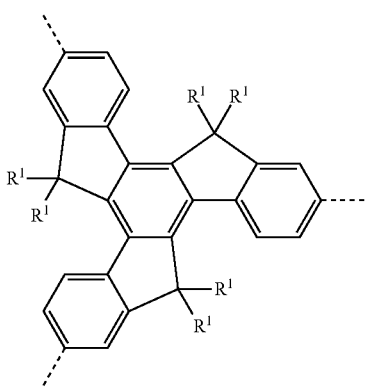

in which:
Y is as defined above and is preferably on each occurrence, identically or differently, in each case a divalent bridge selected from the group consisting of $C(R^1)_2$, $Si(R^1)_2$, O, S, $N(R^1)$ and $P(R^1)$, particularly preferably selected from the group consisting of $C(R^1)_2$, S and $N(R^1)$;
$R^1$ is as defined above, preferably is selected on each occurrence, identically or differently, particularly preferably identically, from the group consisting of H, F, a straight-chain alkyl group having 1 to 6 C atoms, preferably methyl, where one or more H atoms may be replaced by F, and phenyl and naphthyl, preferably phenyl, each of which may be substituted by one or more radicals $R^2$, preferably methyl, but is particularly preferably unsubstituted, and a combination of these systems, where two or more adjacent substituents $R^1$ may also form a mono- or polycyclic, aliphatic or aromatic ring system with one another;

where each of the above groups may furthermore in each case be substituted by one or more radicals $R^1$, but is preferably not further substituted; and where the symbol " ---- " in the above formulae stands for the respective single bond from $Ar_1$ to one of the two nitrogen atoms shown in formula (1);

if a group X is bonded to the unit $Ar_1$, this is preferably bonded at the position which is adjacent to the bond to the nitrogen.

If $Ar_1$ is selected from groups (49) to (51) mentioned above, the index n stands for 2.

In a further preferred embodiment of the invention, $Ar_1$ is a tetravalent group of the formula (52)

formula (52)

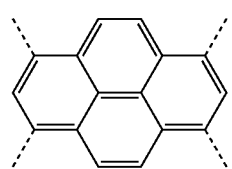

where the symbol " ---- " in the above formulae stands for the respective single bond from $Ar_1$ to one of the two nitrogen atoms shown in formula (1);

if a group X is bonded to the unit $Ar_1$, this is preferably bonded at the position which is adjacent to the bond to the nitrogen.

If $Ar_1$ is a group of the formula (52), the index n stands for 3.

The indices m1 to m6 are 0 or 1, where at least one of the indices m1, m3, m4 and/or m6 is 1. Preferably, at least two of the indices m1 to m6 are equal to 1.

The following particularly preferably applies to the indices m1 to m6:

m1=m6=1 and m2=m3=m4=m5=0; or m1=m4=1 and m2=m3=m5=m6=0; or m1=m2=m4=m5=1 and m3=m6=0; or m1=m2=m5=m6=1 and m3=m4=0; or m1=m2=1 and m3=m4=m5=m6=0; or m1=1 and m2=m3=m4=m5=m6=0; or m2=m3=m4=m5=1 and m1=m6=0; or m3=m4=1 and m1=m2=m5=m6=0.

Particular preference is given to compounds of the formula (2) given above in which $Ar_1$ stands for a group of the formulae (16) to (48). Particular preference is given to compounds in which X simultaneously stands for $C(R^1)_2$, where X is then bonded to the carbon atom which is adjacent to the bond to the nitrogen. Very particular preference is given to compounds in which the above-mentioned preferred embodiments furthermore apply simultaneously to the indices m1 to m6.

Examples of preferred compounds of the formula (1) are structures (1) to (110) depicted below.

(1) 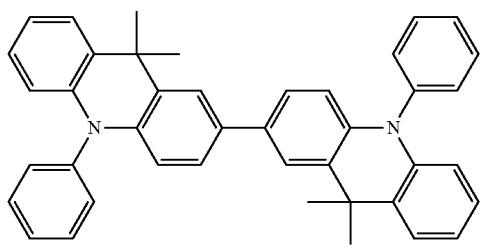
(2) 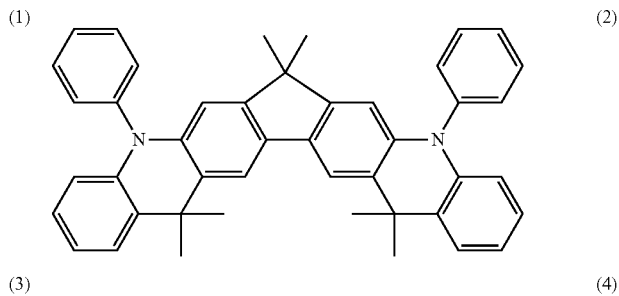
(3) 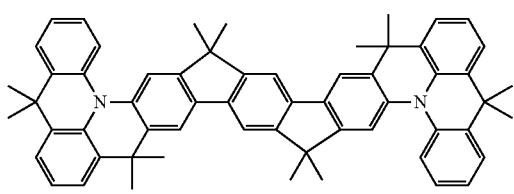
(4) 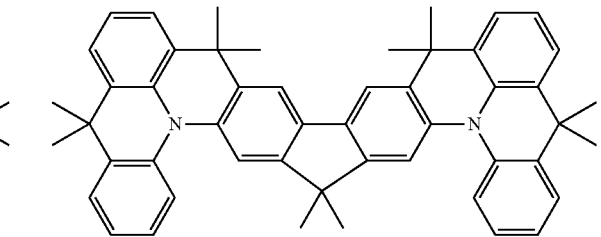
(5) 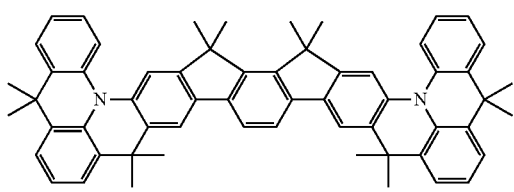
(6) 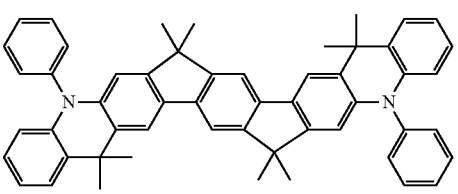
(7) 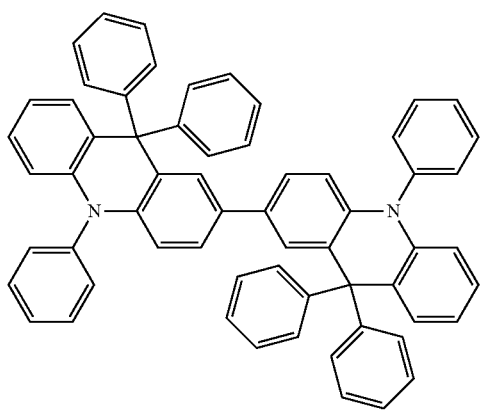
(8) 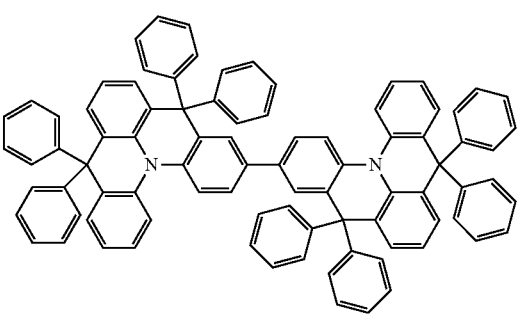
(9) 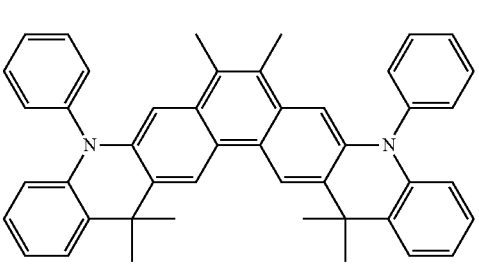
(10) 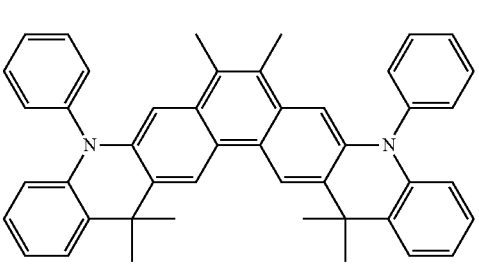

-continued
(11)
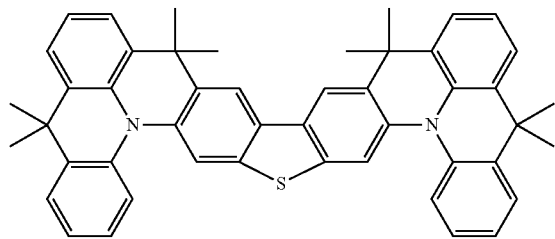
(12)
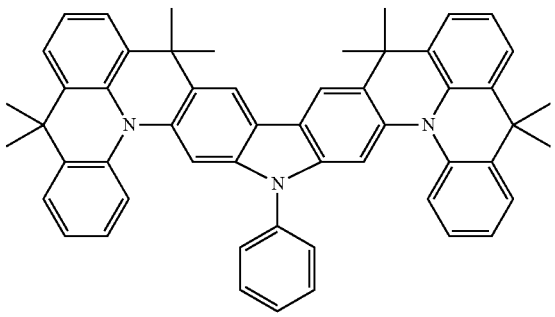
(13)
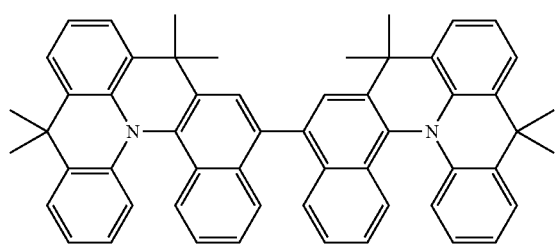
(14)
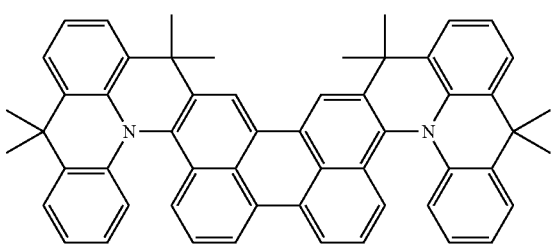
(15)
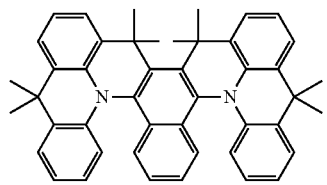
(16)
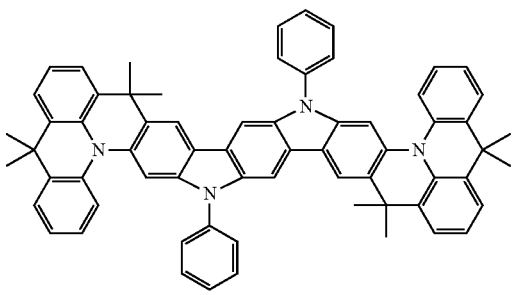
(17)
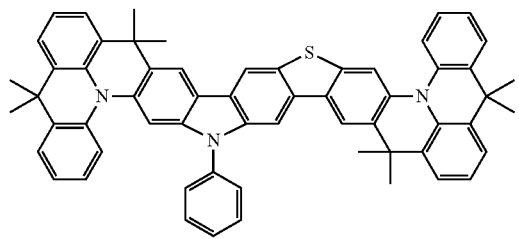
(18)
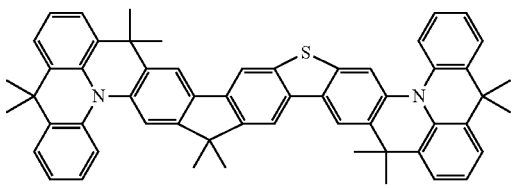
(19)
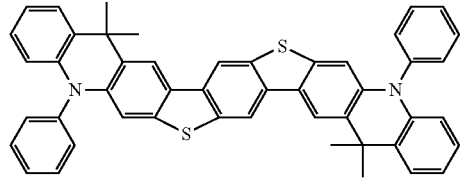
(20)
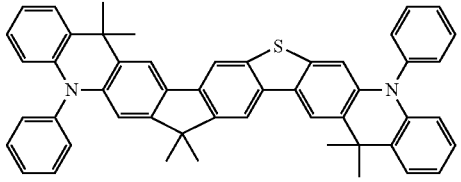
(19)
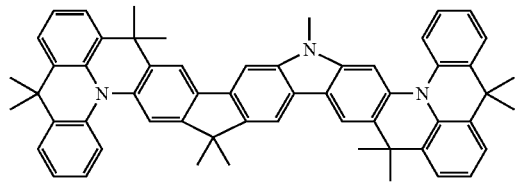
(20)
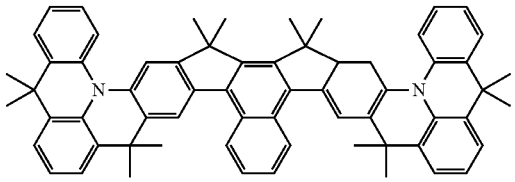

-continued
(21)
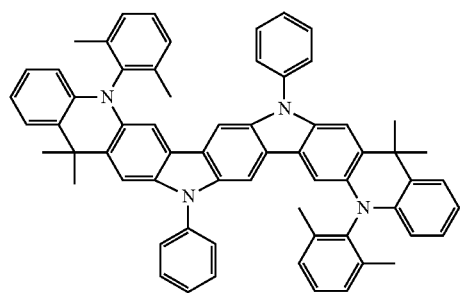
(22)
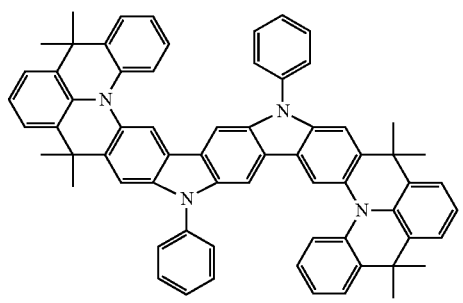
(23)
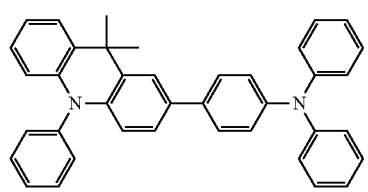
(24)
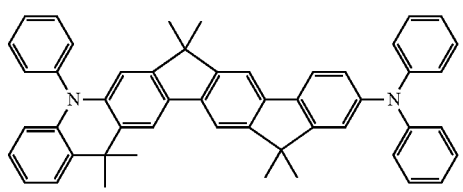
(25)
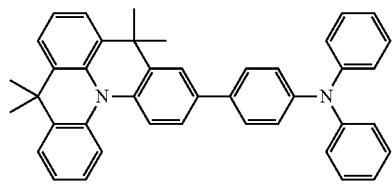
(26)
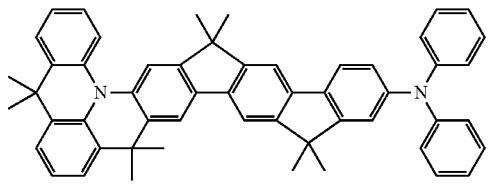
(27)
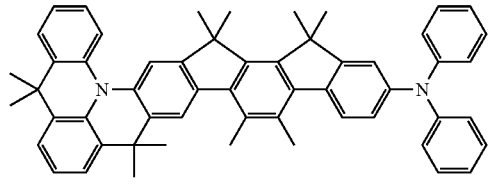
(28)
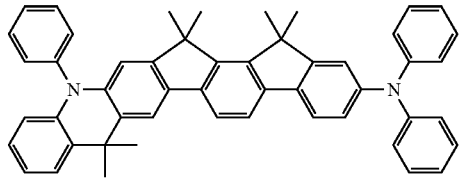
(29)
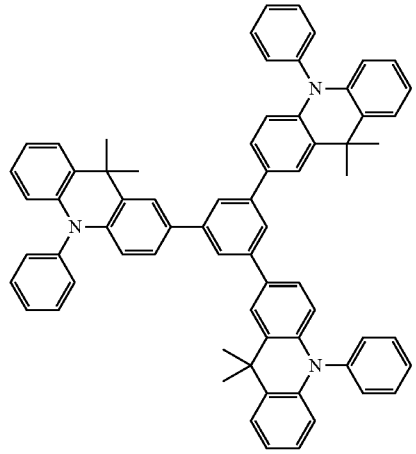
(30)
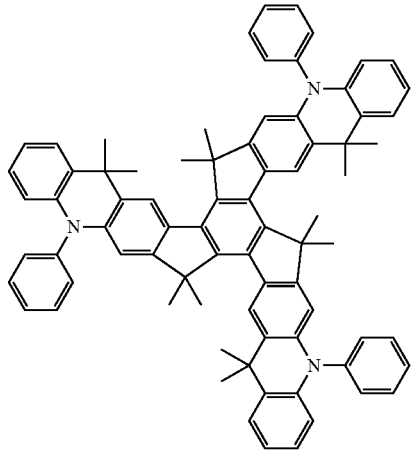

-continued
(31)
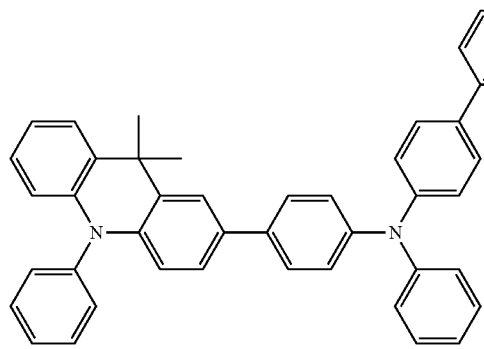
(32)
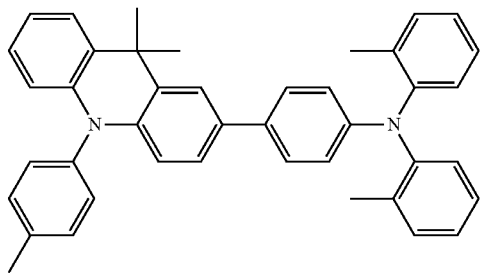
(33)
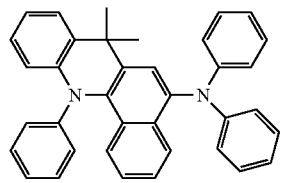
(34)
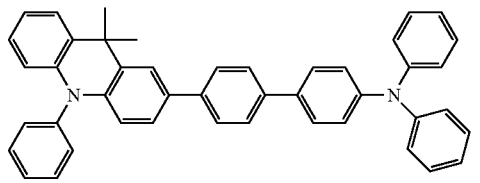
(35)
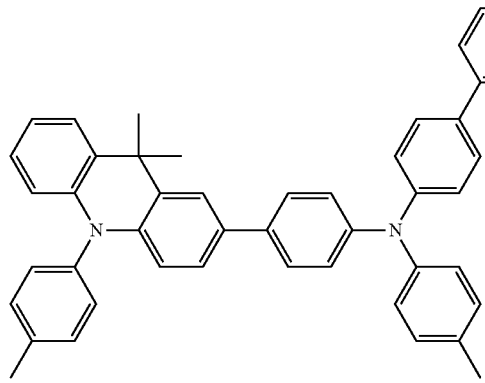
(36)
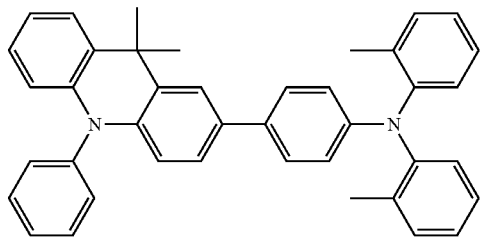
(37)
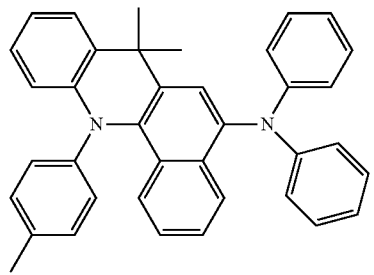
(38)
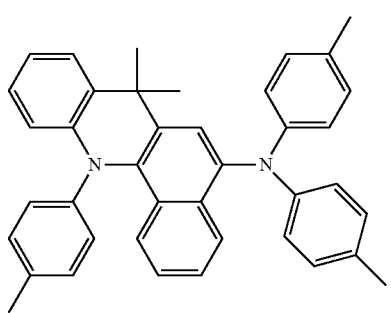
(39)
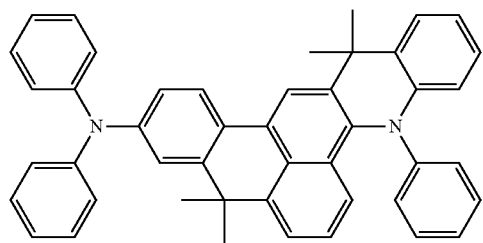
(40)
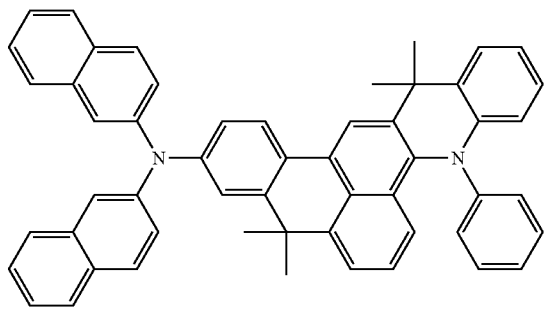

-continued
(41)
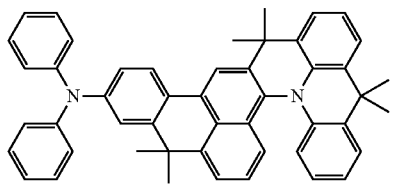
(42)
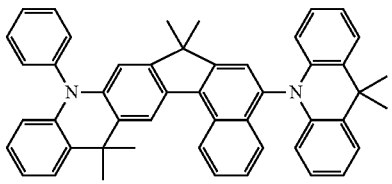
(43)
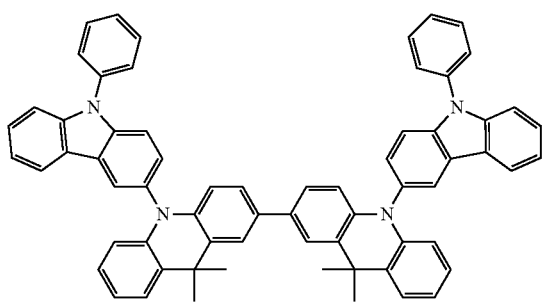
(44)
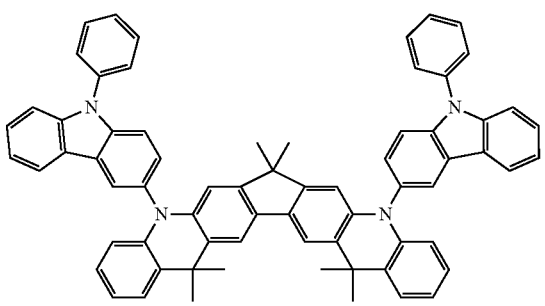
(45)
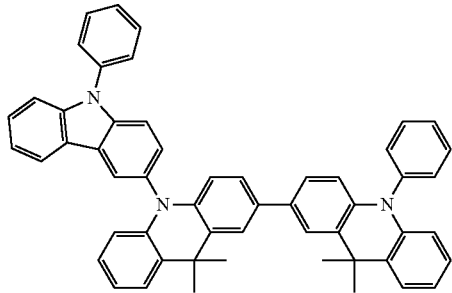
(46)
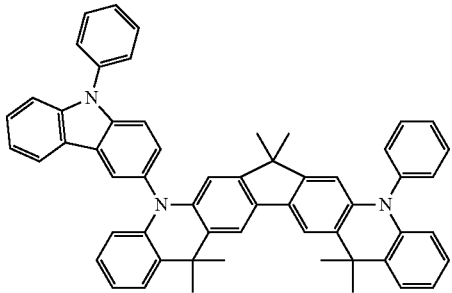
(47)
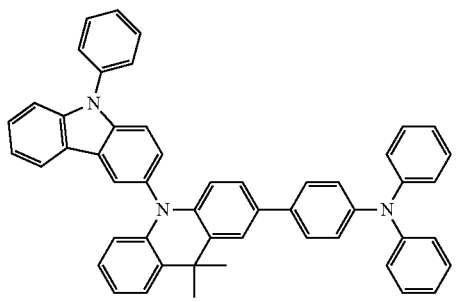
(48)
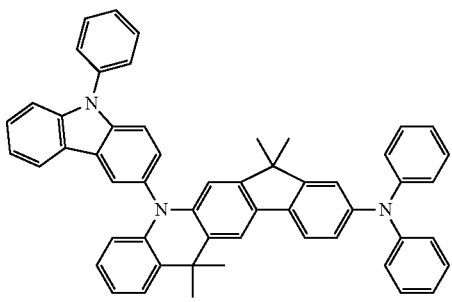
(49)
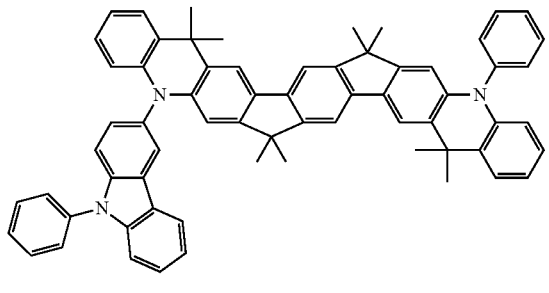
(50)
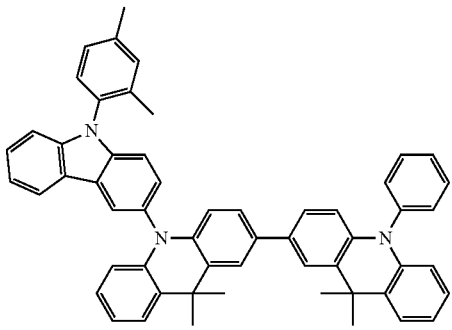

(51)
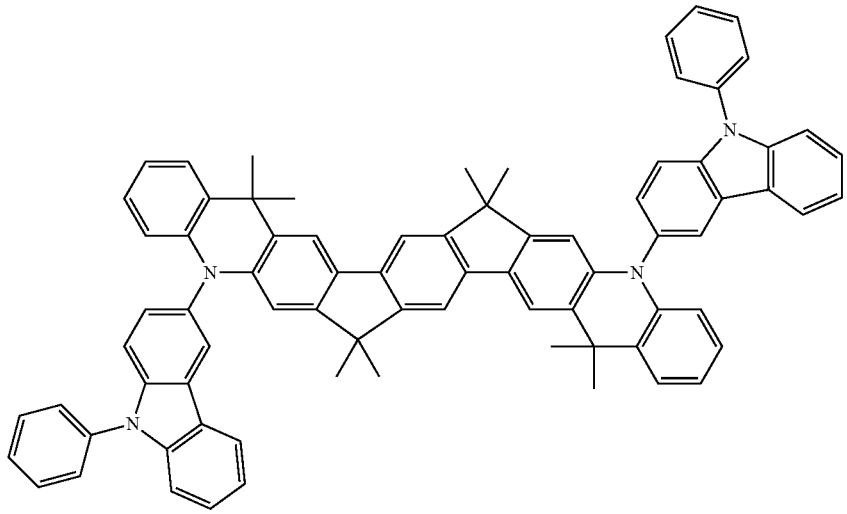
(52)
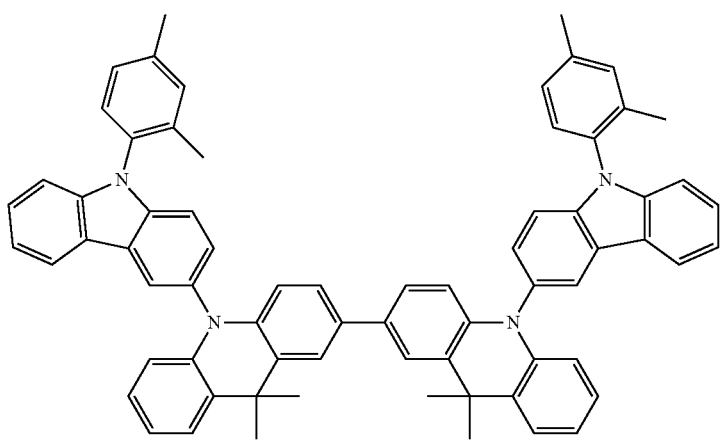
(53)
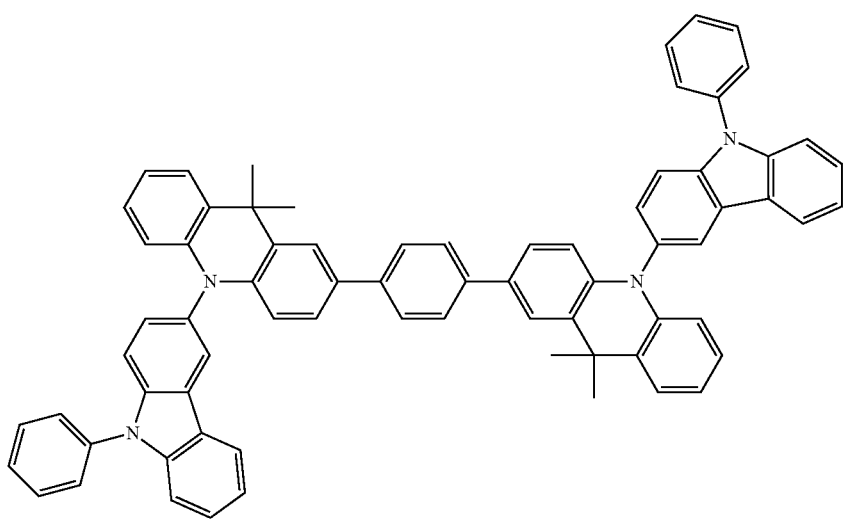

(54)
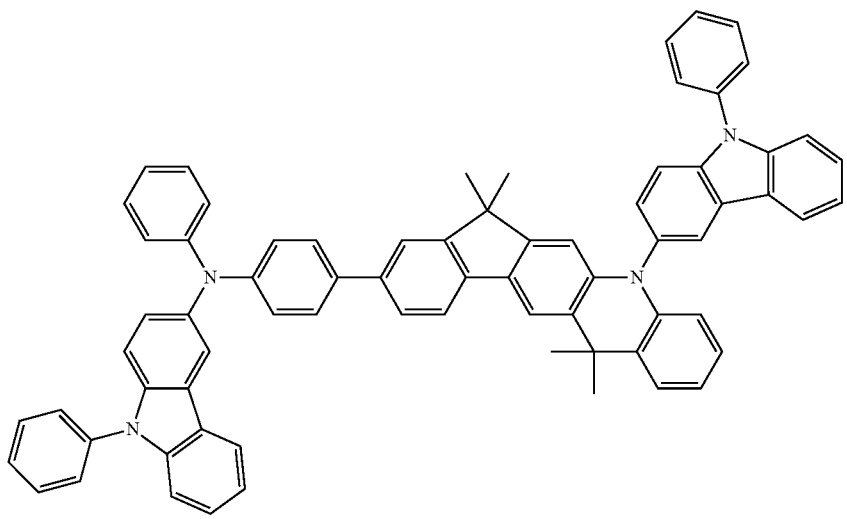
(55)
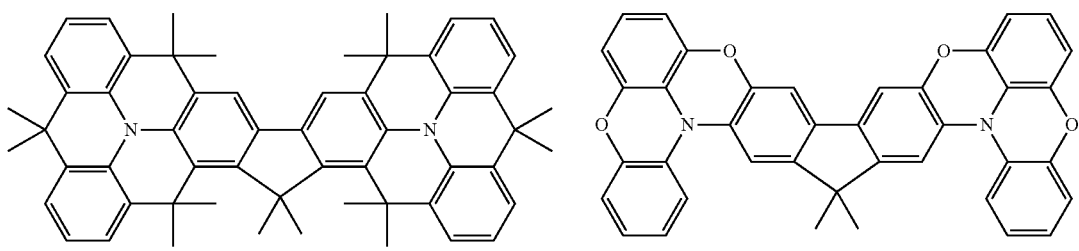
(56)
(57)
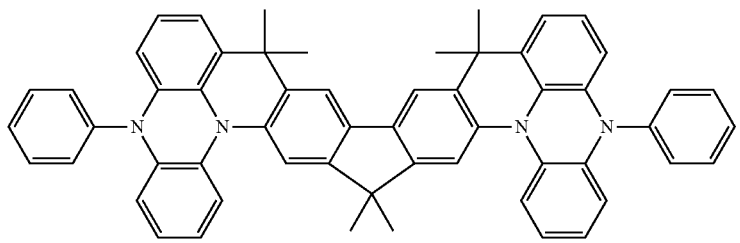
(58)
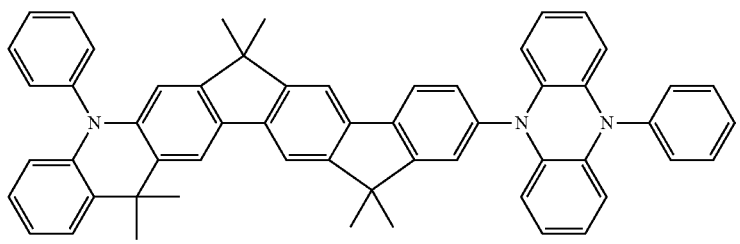
(59)
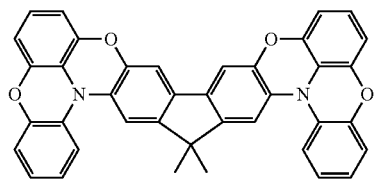
(60)
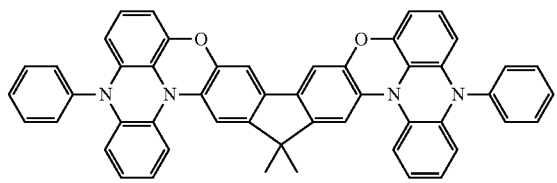

-continued
(61)
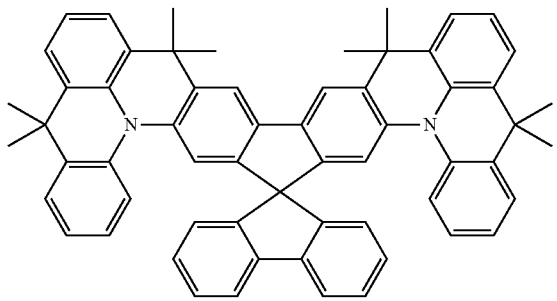
(62)
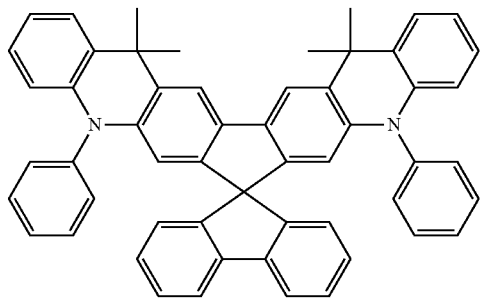
(63)
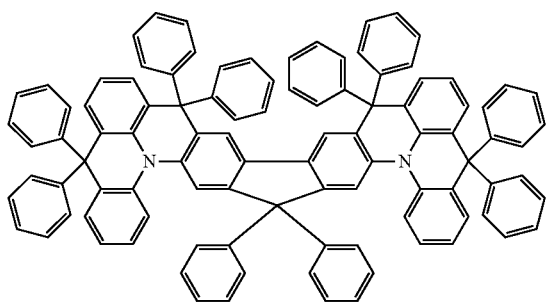
(64)
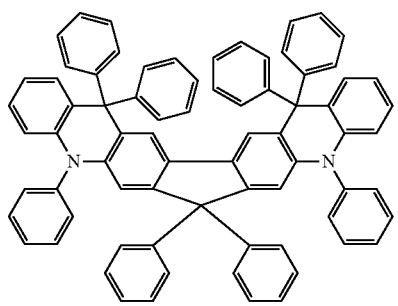
(65)
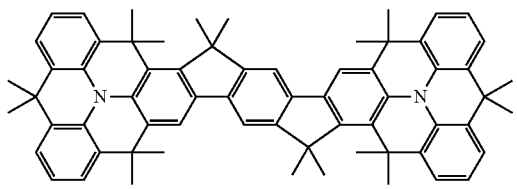
(66)
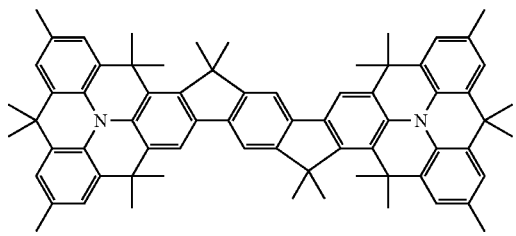
(67)
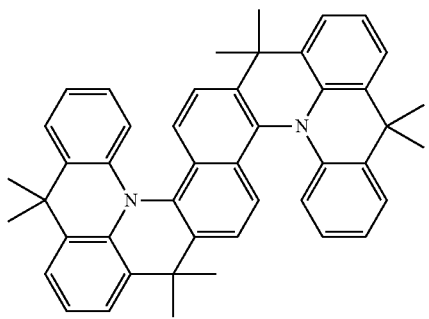
(68)
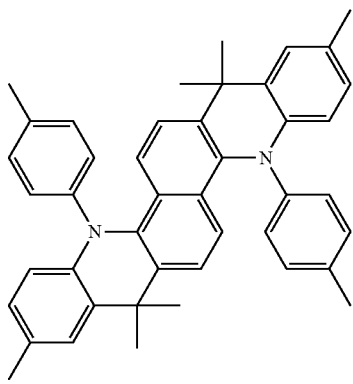

(69)
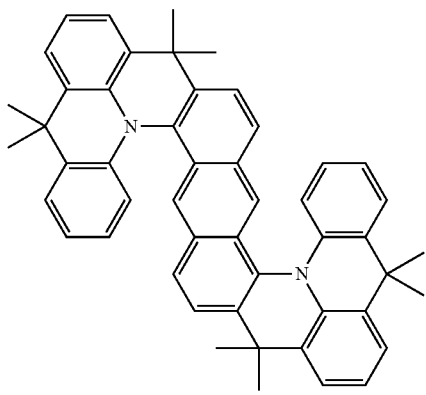
(70)
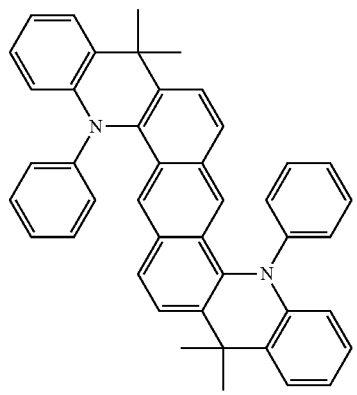
(71)
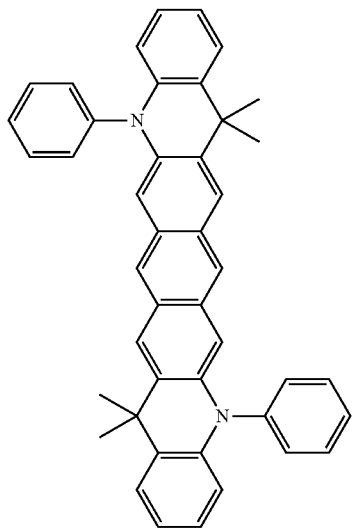
(72)
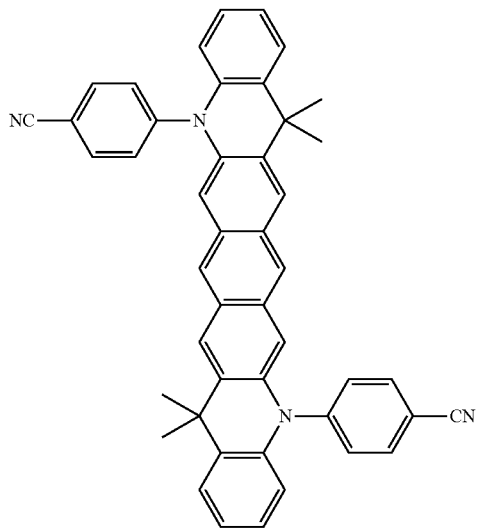
(73)
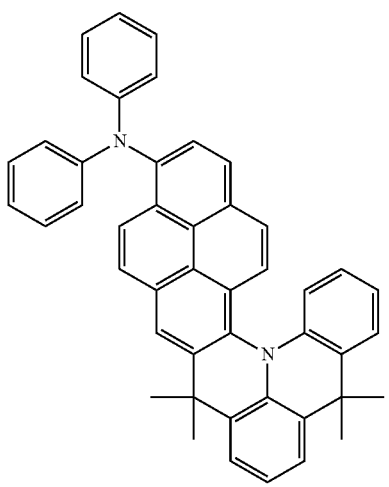
(74)
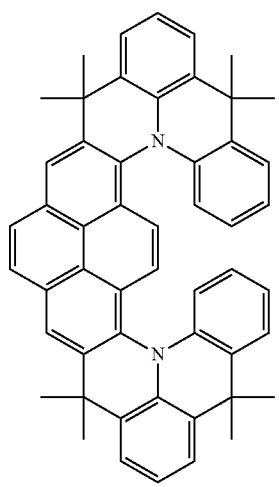

-continued
(75)
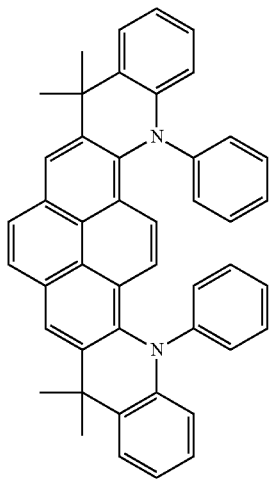
(76)
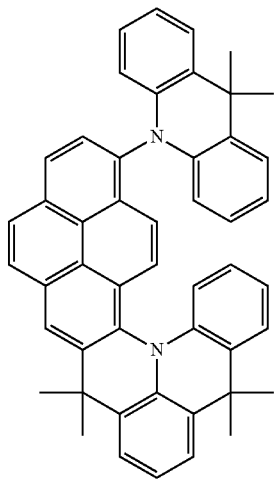
(77)
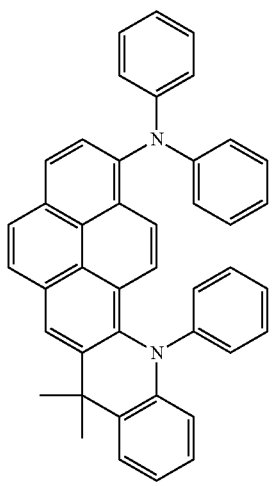
(78)
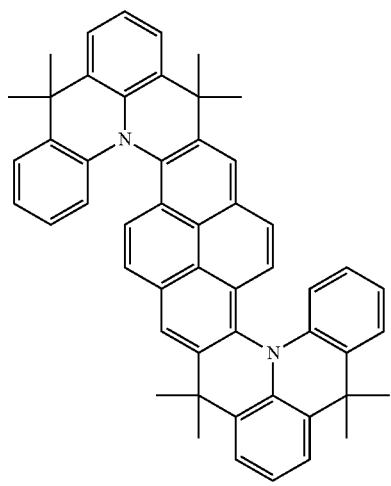
(79)
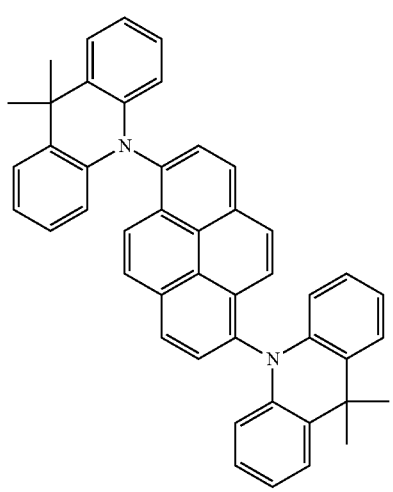
(80)
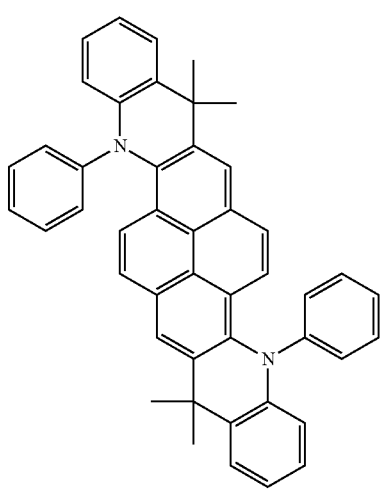

-continued
(81) 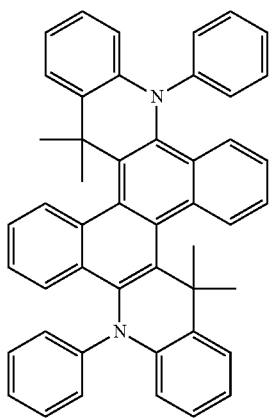
(82) 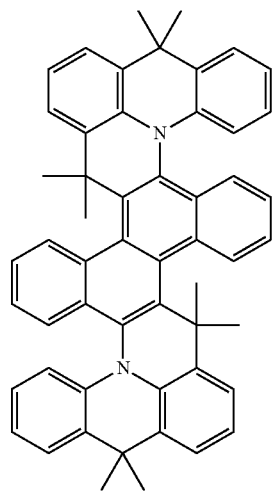
(83) 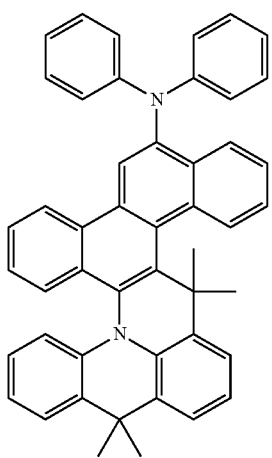
(84) 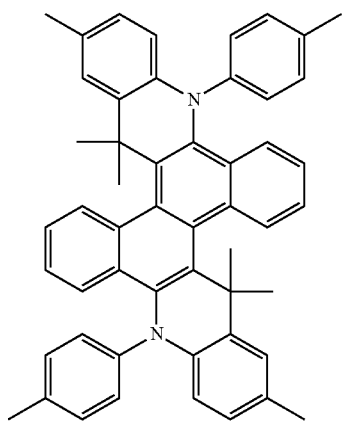
(85) 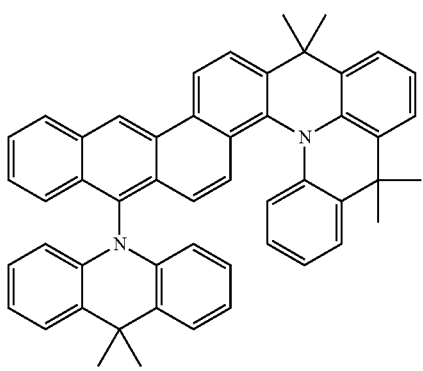
(86) 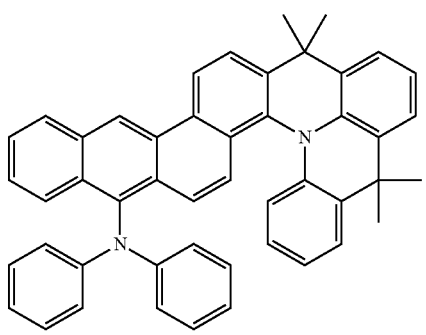
(87) 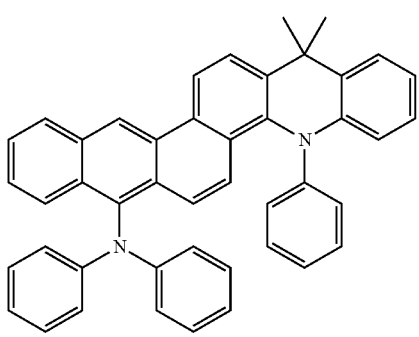
(88) 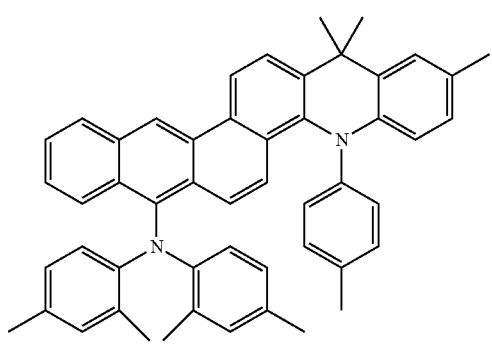

-continued
(89)
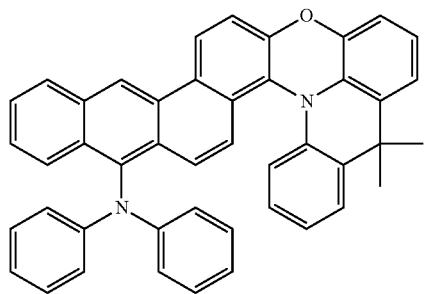
(90)
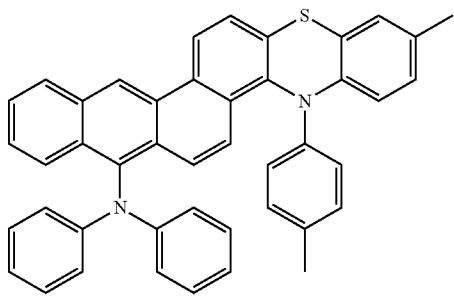
(91)
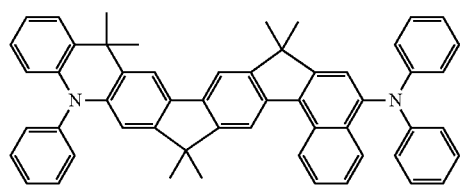
(92)
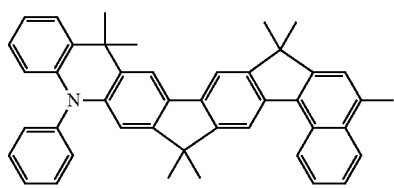
(93)
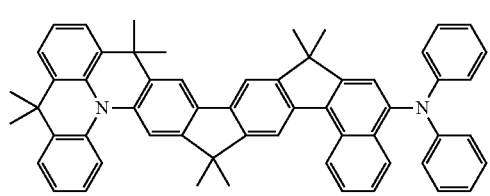
(94)
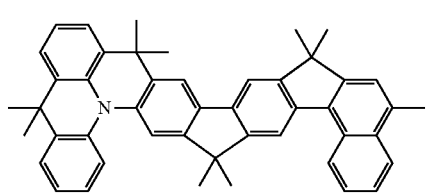
(95)
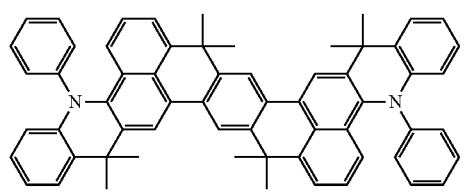
(96)
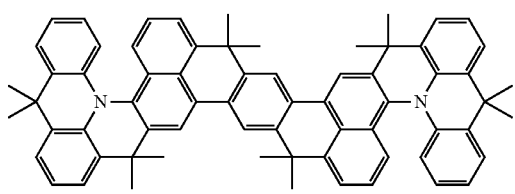
(97)
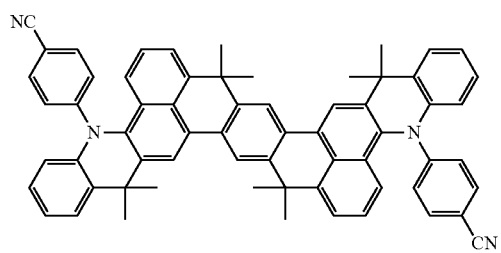
(98)
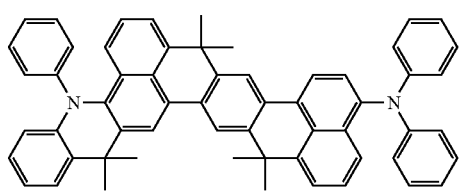
(99)
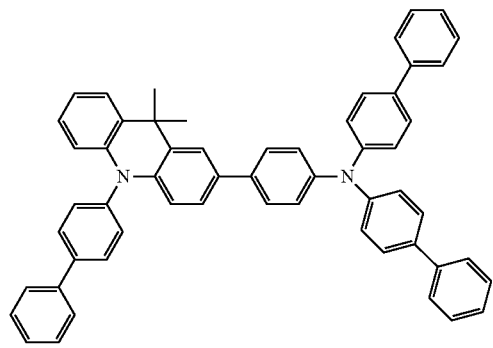
(100)
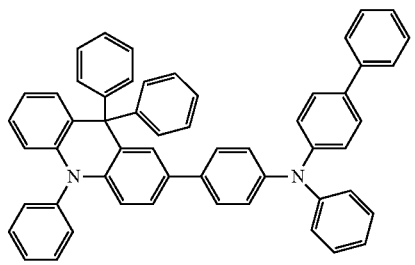

-continued
(101)
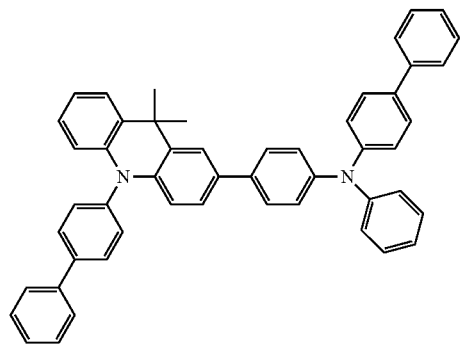
(102)
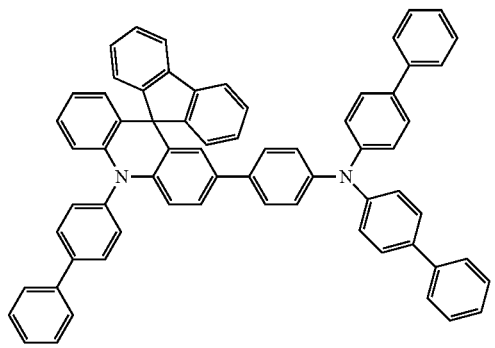
(103)
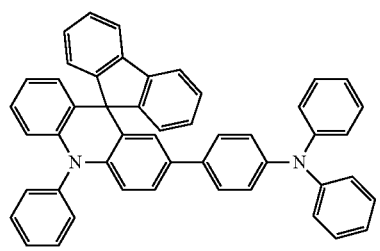
(104)
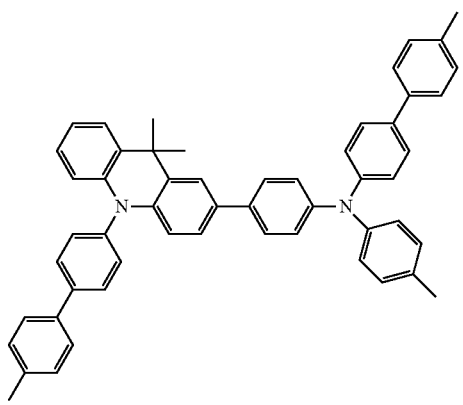
(105)
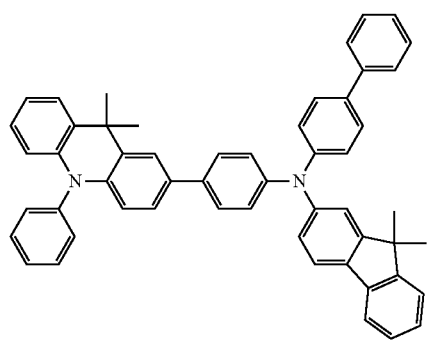
(106)
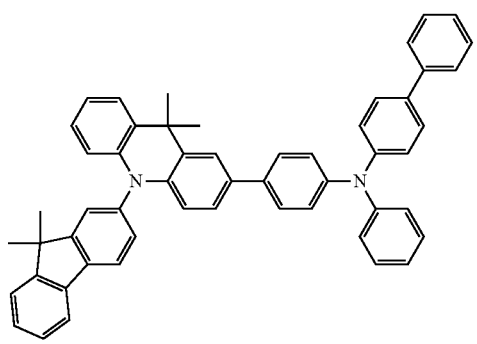
(107)
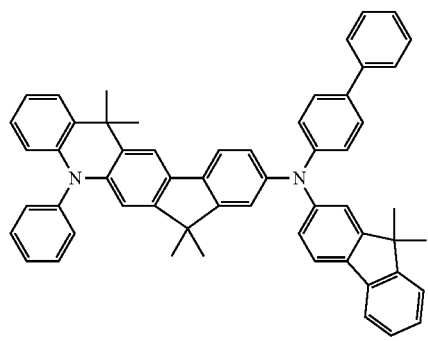
(108)
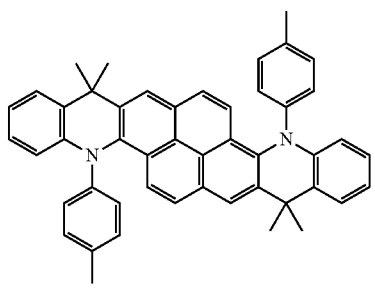

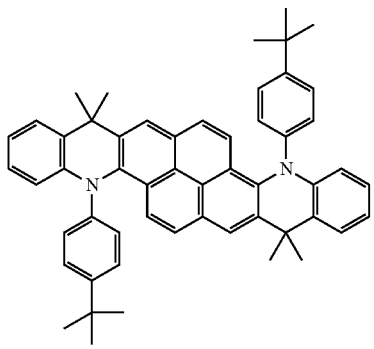
(109)

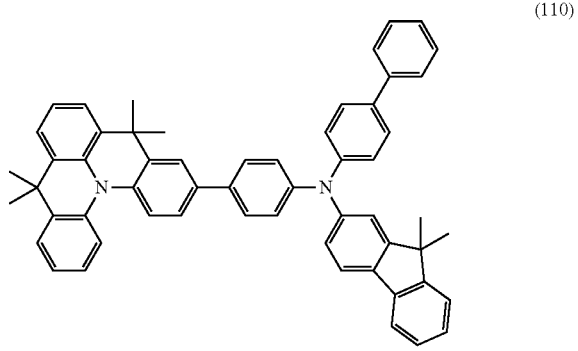
(110)

The compounds according to the invention can be obtained by synthetic steps known to the person skilled in the art, such as, for example, Hartwig-Buchwald couplings and acid-catalysed ring-closure reactions. Thus, for example, the group $Ar_1$ which is substituted by reactive leaving groups, for example halogens, in particular Br or I, can be coupled to an arylamine which is substituted in the ortho-position by a carboxylate group, in a Hartwig-Buchwald coupling. The carboxylate group can then be converted by the addition reaction of an organometallic reagent, for example an organolithium compound or a Grignard reagent, into the corresponding alcohol, which undergoes an acid-catalysed ring-closure reaction with $Ar_1$. In a final step, a further aromatic group can be coupled to the nitrogen in a Hartwig-Buchwald coupling. The reaction conditions which are usually selected for these reactions are generally known to the person skilled in the art of organic synthesis. The synthesis is shown by way of example in Schemes 1 and 2 for two compounds of the formula (1). However, the person skilled in the art will be able to employ other groups $Ar_1$ or other aromatic amines in order to synthesise further compounds of the formula (1) in a simple manner without an inventive step.

Scheme 1:

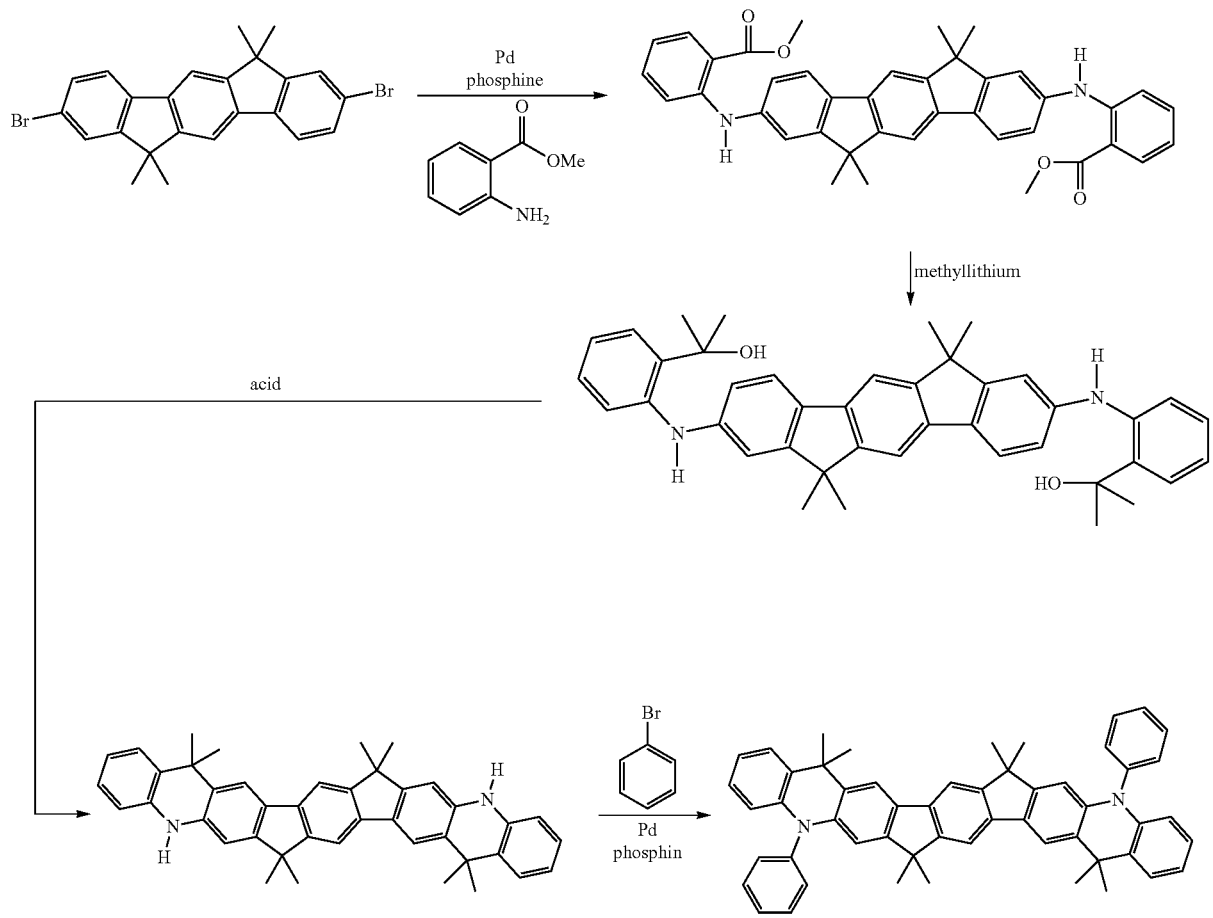

Scheme 2:

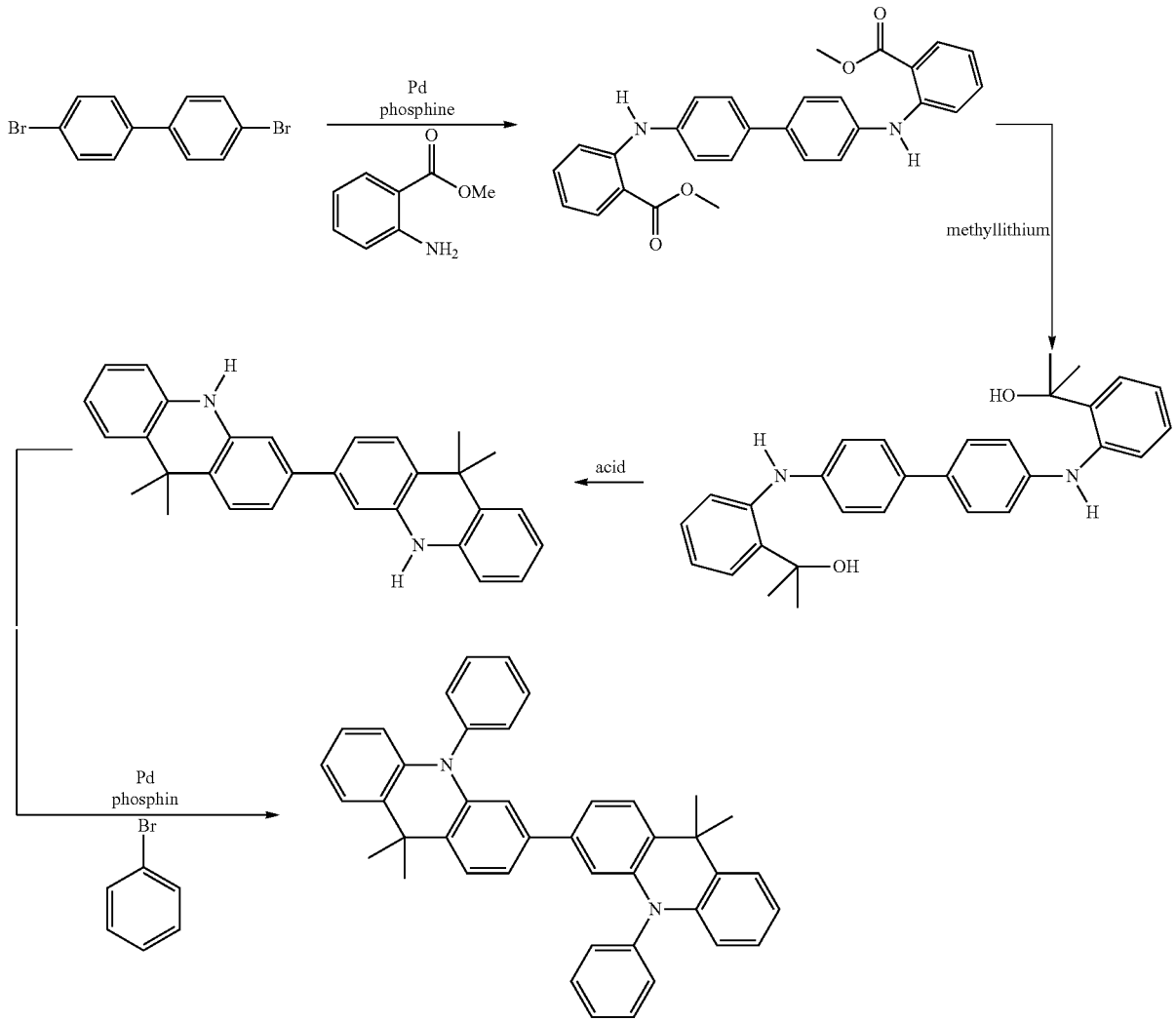

The present invention furthermore relates to a process for the preparation of compounds of the formula (1), comprising the following reaction steps:
a) coupling of a suitably substituted group $Ar_1$ to an arylamine which is suitably substituted in the ortho-position and where the aryl group corresponds to the group $Ar_2$ or $Ar_3$ or $Ar_4$ or $Ar_5$; and
b) ring-closure reaction of the substituent in the ortho-position of the arylamine with the group $Ar_1$.

These process steps can optionally be followed by a further coupling reaction in order to introduce a further group $Ar_2$ or $Ar_3$ or $Ar_4$ or $Ar_5$ or this coupling reaction can be carried out before the ring-closure reaction.

The compounds according to the invention may also be part of an oligomer, polymer or dendrimer. In this case, the bond to a substituent on the compound according to the invention is replaced by a bond to the oligomer, polymer or dendrimer. The present invention therefore furthermore relates to oligomers, polymers and dendrimers containing one or more of the compounds mentioned above.

The compounds of the formula (1) according to the invention are suitable for use in electronic devices, in particular in organic electroluminescent devices (OLEDs). Depending on the substitution, the compounds are employed in various functions and layers.

The invention therefore furthermore relates to the use of the compounds of the formula (1) according to the invention in electronic devices. The electronic devices here are preferably selected from the group consisting of organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and particularly preferably organic electroluminescent devices (OLEDs).

The invention still furthermore relates to electronic devices comprising at least one compound of the formula (1). The electronic devices here are preferably selected from the devices mentioned above. Particular preference is given to organic electroluminescent devices comprising an anode, a cathode and at least one emitting layer, characterised in that at least one organic layer, which may be an emitting layer, a hole-transport layer or another layer, comprises at least one compound of the formula (1).

Apart from the cathode, anode and emitting layer, the organic electroluminescent device may also comprise further layers. These are selected, for example, from in each case one or more hole-injection layers, hole-trans-port layers, hole-blocking layers, electron-transport layers, electron-injection layers, electron-blocking layers, exciton-blocking layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device may also comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. Particular preference is given to three-layer systems, i.e. systems having three emitting layers, where at least one of these layers comprises at least one compound of the formula (1) and where the three layers exhibit blue, green and orange or red emission (for the basic structure see, for example, WO 05/011013). Emitters which have broad-band emission bands and thus exhibit white emission are likewise suitable for white emission.

In a preferred embodiment of the invention, the compounds of the formula (1) are employed as hole-transport material. The compounds are then preferably employed in a hole-transport layer and/or in a hole-injection layer. For the purposes of this invention, a hole-injection layer is a layer which is directly adjacent to the anode. For the purposes of this invention, a hole-transport layer is a layer which is located between the hole-injection layer and the emission layer. If the compounds of the formula (1) are used as hole-transport material, it may be preferred for them to be doped by electron-acceptor compounds, for example by $F_4$-TCNQ or by compounds as described in EP 1476881 or EP 1596445. If the compound of the formula (1) is employed as hole-transport material in a hole-transport layer, the compound can be employed as the pure material, i.e. in a proportion of 100%, in the hole-transport layer or it can be employed in combination with further compounds in the hole-transport layer.

It is preferred in accordance with the invention for the compound of the formula (1) to be employed in an electronic device comprising one or more phosphorescent emitters. The compound here can be used in a hole-transport layer, a hole-injection layer or in the emitting layer, particularly preferably in a hole-transport layer.

Suitable phosphorescent emitter compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters employed are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable. In addition, the person skilled in the art will be able, without an inventive step, to employ further phosphorescent complexes as emitter materials in organic electroluminescent devices comprising the compounds according to the invention.

In a further preferred embodiment of the invention, the compound of the formula (1) is employed as emitting material in an emitting layer. The compounds of the formula (1) are then particularly suitable as emitting material if at least one of the groups $Ar_1$ to $Ar_5$, in particular $Ar_1$, stands for a condensed aromatic or heteroaromatic ring system, in particular having at least three condensed aromatic or heteroaromatic rings. Particularly preferred emitting materials are compounds of the formula (1) in which the group $Ar_1$ stands for an anthracene or a chrysene.

If the compound of the formula (1) is employed as emitting material in an emitting layer, it is preferably employed in combination with a host material. In a system comprising host and dopant, a host material is taken to mean the component which is present in the higher proportion in the system. In a system comprising a host and a plurality of dopants, the host is taken to mean the component whose proportion in the mixture is the highest.

The proportion of the compound of the formula (1) in the mixture of the emitting layer is between 0.1 and 50.0% by vol., preferably between 0.5 and 20.0% by vol., particularly preferably between 1.0 and 10.0% by vol. Correspondingly, the proportion of the host material is between 50.0 and 99.9% by vol., preferably between 80.0 and 99.5% by vol., particularly preferably between 90.0 and 99.0% by vol.

Suitable host materials for this purpose are materials from various classes of substance. Preferred host materials are selected from the classes of the oligoarylenes (for example 2, 2',7,7-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145,239). Particularly preferred host materials are selected from the classes of the oligoarylenes comprising naphthalene, anthracene, benzanthracene and/or pyrene, or atropisomers of these compounds, the ketones, the phosphine oxides and the sulfoxides. Very particularly preferred host materials are selected from the classes of the oligoarylenes comprising anthracene, benzanthracene and/or pyrene, or atropisomers of these compounds. For the purposes of this invention, an oligoarylene is intended to be taken to mean a compound in which at least three aryl or arylene groups are bonded to one another.

Preferred host materials are selected, in particular, from compounds of the formula (53)

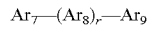   formula (53)

where $Ar_7$, $Ar_8$, $Ar_9$ are on each occurrence, identically or differently, an aryl or heteroaryl group having 5 to 30 aromatic ring atoms, which may be substituted by one or more radicals $R^1$, and $R^1$ has the same meaning as described above, and p can adopt a value of 0, 1, 2 or 3. The group $Ar_8$ in the host materials of the formula (53) particularly preferably stands for anthracene, which may be substituted by one or more radicals $R^1$, and the groups $Ar_7$ and $Ar_9$ are bonded in the 9- and 10-positions. Very particularly preferably, at least one of the groups $Ar_7$ and/or $Ar_9$ is a condensed aryl group selected from 1- or 2-naphthyl, 2-, 3- or 9-phenanthrenyl or 2-, 3-, 4-, 5-, 6- or 7-benzanthracenyl, each of which may be substituted by one or more radicals $R^1$.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds of the formula (1) are necessary for this purpose. High solubility can be achieved through suitable substitution of the compounds.

The compounds according to the invention have the following surprising advantages over the prior art on use in organic electroluminescent devices:
1. On use of the compounds according to the invention as hole-trans-port material in a hole-transport and/or hole-injection layer, lower use voltages and operating voltages are required than with compounds in accordance with the prior art which do not contain a bridging group X. The use of the compounds according to the invention thus results in significantly higher power efficiency of the OLED.
2. The compounds according to the invention are particularly suitable for use in electronic devices comprising phosphorescent emitters, where they result in improvements in lifetime and power efficiency of the devices.
3. A further advantage on use of the compounds according to the invention as hole-transport material in a hole-transport and/or hole-injection layer is the reduced voltage difference between thin (20 nm) and thick (110 nm) hole-transport layers. Thicker hole-transport layers can thus be used with the compounds according to the invention without a considerable loss in power efficiency. This is important, since the optical coupling-out efficiency is crucially controlled by variation of the layer thickness of the hole-transport layer. Even improvements in the region of 0.1V are regarded as a significant advance here.
4. The compounds according to the invention also exhibit very good efficiency and lifetime on use of the compounds according to the invention as dopant in an emitting layer.
5. The processability of the compounds according to the invention is significantly improved compared with materials in accordance with the prior art which do not contain a bridging group X. Thus, the compounds according to the invention exhibit a lower tendency to clog the vapour-deposition source under the same vapour-deposition conditions. The compounds according to the invention are thus significantly more suitable for use in mass production than materials in accordance with the prior art.

The invention is explained in greater detail by the following examples, without wishing to restrict it thereby.

WORKING EXAMPLES

The following syntheses are carried out, unless indicated otherwise, under a protective-gas atmosphere in dried solvents. The starting materials can be purchased from ALDRICH.

Example 1:

Synthesis of Example Compound 1 a) Bis[N-(2-carboxymethylphenyl)]-6,6,12,12-tetramethyl-6-12-dihydroindeno[1,2b]fluorine diamine

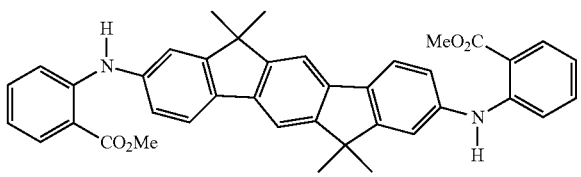 [SMILES: COC(=O)c1ccccc1Nc1ccc2c(c1)C(C)(C)c1cc3c(cc1-2)C(C)(C)c1cc(Nc2ccccc2C(=O)OC)ccc1-3]

35.51 g (234.9 mmol) of methyl anthranilate are dissolved in 500 ml of toluene, and the solution is thoroughly degassed. 50.0 g (106.8 mmol) of 6,6,12,12-tetramethyl-6-12-dihydroindeno[1,2b]fluorenyl dibromide, 2.1 g (10.7 mmol) of 4,5-bis(diphenylphosphino)-9,9-dimethylxanthene, 1.19 g (5.34 mmol) of $Pd(OAc)_2$ and 76.5 g (234.9 mmol) of $Cs_2CO_3$ are added, and the mixture is subsequently degassed and stirred at 100° C. under a protective-gas atmosphere for 24 h. The solids are subsequently filtered off through Celite, and the organic phase is washed with water, dried over $MgSO_4$ and evaporated. The crude product is washed by stirring with hot heptane, giving 56 g (86%) of the product as a yellow solid.

b) Bis[N-(2-(1-methyl-1-hydroxyethyl)phenyl)]-6,6,12,12-tetramethyl-6-12-dihydroindeno[1,2b]fluorine diamine

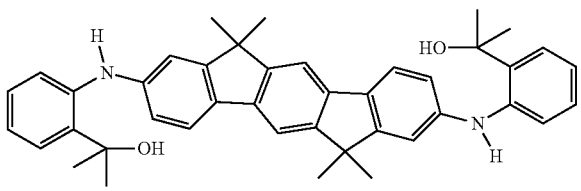 [SMILES: CC(C)(O)c1ccccc1Nc1ccc2c(c1)C(C)(C)c1cc3c(cc1-2)C(C)(C)c1cc(Nc2ccccc2C(C)(C)O)ccc1-3]

56.0 g (92.0 mmol) of the compound from a) are dissolved in 1200 ml of dried THF, and the solution is degassed. The solution is cooled to −78° C., and 334.53 ml (736.0 mmol) of a 2.2 M solution of methyllithium in diethyl-ether are added over the course of 40 min. The mixture is allowed to warm to −40° C. over the course of 1 h, and the reaction is monitored by TLC. When the reaction is complete, it is quenched carefully with MeOH at −30° C. The reaction solution is concentrated to 1/3, 1 l of methylene chloride is added, the mixture is washed, and the organic phase is dried over MgSO$_4$ and evaporated. The yellow crude product is not purified further and is employed directly in the next step.

c) Bisacridine Compound

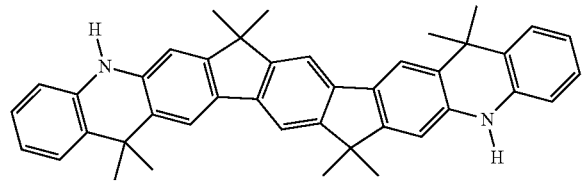 [SMILES: CC1(C)c2ccccc2Nc2cc3c(cc21)-c1cc2c(cc1C3(C)C)-c1cc3c(cc1C2(C)C)Nc1ccccc1C3(C)C]

55.0 g (90.3 mmol) of bis[N-(2-(1-methyl-1-hydroxyethyl)phenyl)]-6,6,12,12-tetramethyl-6,12-dihydroindeno[1,2b]fluorine diamine are dissolved in 1200 ml of degassed toluene, and a suspension of 70 g of polyphosphoric acid and 50 ml of methanesulfonic acid is added, and the mixture is heated at 60° C. for 1 h. The batch is cooled, and water is added. A solid precipitates out and is dissolved using methylene chloride/THF (1:1). The solution is carefully rendered alkaline using 20% NaOH, and the phases are separated and dried over MgSO$_4$. The solid obtained is washed by stirring with heptane, giving 36 g (70%) of the product, which can be employed further directly.

d) Example Compound 1

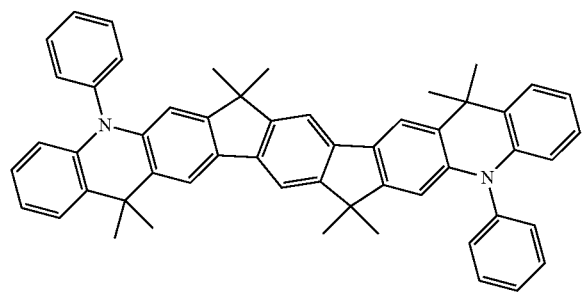 [SMILES: CC1(C)c2cc3c(cc2-c2cc4c(cc21)N(c1ccccc1)c1ccccc1C4(C)C)C(C)(C)c1cc2c(cc1-3)C(C)(C)c1ccccc1N2c1ccccc1]

50.0 g (87.3 mmol) of the bisacridine from c) and 34.75 ml (261.8 mmol) of bromobenzene are dissolved in 2500 ml of degassed toluene, and the solution is then degassed. Tri-tert-butylphosphine (6.11 ml, 1M solution in toluene) is added, 685.9 mg (3.05 mmol) of Pd(OAc)$_2$ and 25.1 g (209.4 mmol) of sodium tert-butoxide are added, and the mixture is then briefly degassed and heated under reflux for 3 h. The reaction solution is washed with water, and the precipitated solid and the organic phase are combined, evaporated and dried azeotropically a number of times using toluene, giving 49.1 g (77%) of a yellow solid, which is purified further by means of Soxhlet extraction and crystallisation from NMP.

Example 2:

Synthesis of Example Compound 2 a) Bis[1,1'-N-(2-carboxymethylphenyl)]-4,4'-biphenyl diamine

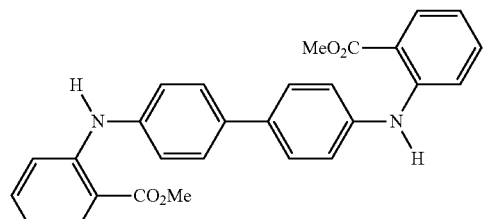

100.0 g (320.5 mmol) of 4,4'-dibromobiphenyl and 106.6 g (705.1 mmol) of methyl anthranilate are dissolved in 1200 ml of degassed toluene, the solution is subsequently degassed, and 229.7 g (705.1 mmol) of Cs$_2$CO$_3$, 3.59 g (16.03 mmol) of Pd(OAc)$_2$ and 6.29 g (32.05 mmol) of 4,5-bis(di-phenylphosphino)-9,9-dimethylxanthene are added. The reaction mixture is stirred at an internal temperature of 100° C. for 48 h. The cooled reaction solution is filtered through aluminium oxide, washed with water, dried over MgSO$_4$ and evaporated. The crude product is washed by stirring with heptane, giving 129 g (89%) of the product as a white solid.

b) Bis[1,1% N-(2-(1-methyl-1-hydroxyethyl)phenyl)]-4,4'-biphenyl diamine

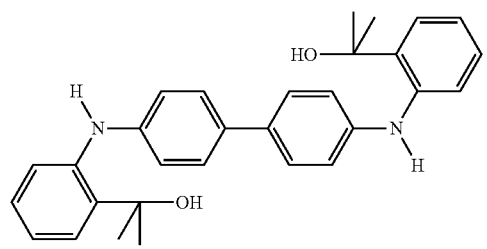 [SMILES: CC(C)(O)c1ccccc1Nc1ccc(-c2ccc(Nc3ccccc3C(C)(C)O)cc2)cc1]

64.5 g (142.5 mmol) of bis[1,1'-N-(2-(carboxymethyl)phenyl)]-4,4'-biphenyl diamine are dissolved in 1500 ml of dry THF, the solution is cooled to −78° C., and 518.3 ml of methyllithium (2.2 M in diethyl ether) are added dropwise. The mixture is slowly warmed to −40° C. and stirred for a further 1 h. The reaction is quenched slowly and carefully with MeOH at −30° C., and the reaction solution is concentrated to 1/3. Toluene is added, and the mixture is washed with water, dried over MgSO$_4$ and evaporated. The conversion is quantitative, and the reaction product can be employed directly in the next reaction.

c) Bisacridine Compound

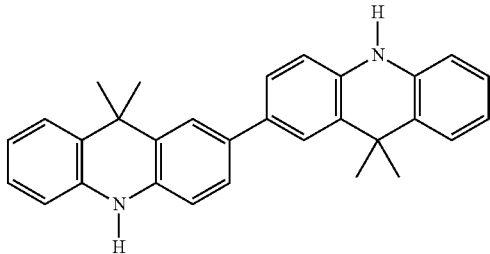 [SMILES: CC1(C)c2ccccc2Nc2ccc(-c3ccc4c(c3)C(C)(C)c3ccccc3N4)cc21]

61.6 g (136.1 mmol) of bis[1,1'-N-(2-(1-methyl-1-hydroxyethyl)phenyl)]-4,4'-biphenyl diamine are suspended in 1200 ml of degassed toluene, and 110.9 g of polyphosphoric acid and 77.2 ml of methanesulfonic acid are added at room temperature. The mixture is subsequently heated to 50° C. and stirred at this temperature for 2 h. The cooled toluene phase is decanted off, the precipitated solid is dissolved using methanol/THF (1:1), the solution is added to ice-water, and the mixture is carefully adjusted to pH=8 using 20% NaOH. The organic phase (heterogeneous) is separated off, evaporated and dried azeotropically using toluene. The conversion is quantitative, and the crude product can be employed directly in the next reaction.

d) Example Compound 2

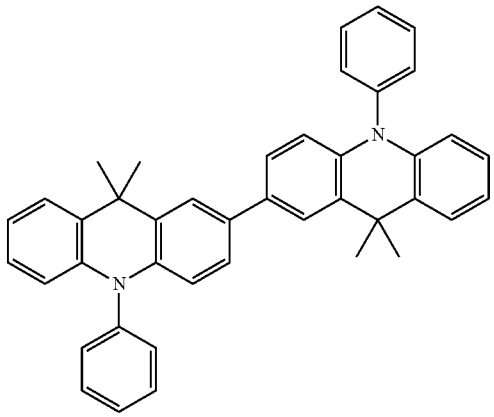 [SMILES: CC1(C)c2ccccc2N(c2ccccc2)c2ccc(-c3ccc4c(c3)C(C)(C)c3ccccc3N4c3ccccc3)cc21]

54.0 g (129.6 mmol) of the bisacridine from c) and 40.95 ml (388.9 mmol) of bromobenzene are dissolved in 2000 ml of degassed toluene, the solution is subsequently degassed, 9.07 ml (9.07 mmol, 1M solution in toluene) of tri-tert-butylphosphine, 611.18 mg (2.72 mmol) of Pd(OAc)$_2$ and 37.3 g (388.9 mmol) of sodium tert-butoxide are added, and the mixture is heated under reflux for 2.5 h. The cooled batch is washed with water, dried over MgSO$_4$ and evaporated, giving 69 g (93%) of a white solid, which is purified further by means of Soxhlet extraction and crystallisation from toluene.

Example 3:

Synthesis of Example Compound 3 a) Bis[2,7-N-(2-carboxymethylphenyl)]-9,9-dimethylfluorine diamine

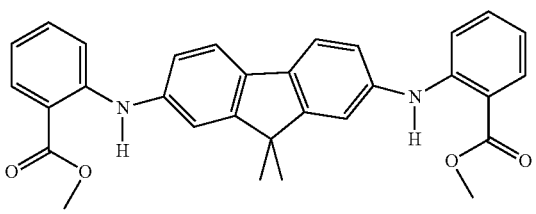 [SMILES: COC(=O)c1ccccc1Nc1ccc2c(c1)C(C)(C)c1cc(Nc3ccccc3C(=O)OC)ccc1-2]

137.94 g (372.21 mmol) of 2,7-dibromo-9,9-dimethylfluorene and 105.79 ml (818.87 mmol) of methyl anthranilate are dissolved in 2000 ml of degassed toluene. 266.79 g (818.87 mmol) of Cs$_2$CO$_3$, 4.17 g (18.61 mmol) of Pd(OAc)$_2$ and 7.31 g (37.22 mmol) of 4,5-bis(diphenyl-phosphino)-9,9-dimethylxanthene (xantphos) are added. The reaction mixture is heated under reflux for 9 h and then allowed to cool, and ethyl acetate is added. The mixture is washed with water, dried over MgSO$_4$ and evaporated in a rotary evaporator. Washing by stirring with hot heptane gives 161.4 g (88%) of the product as a yellow solid.

b) Bis[2,7-N-(2-(1-methyl-1-hydroxyethyl)phenyl)]-9,9-dimethylfluorene diamine

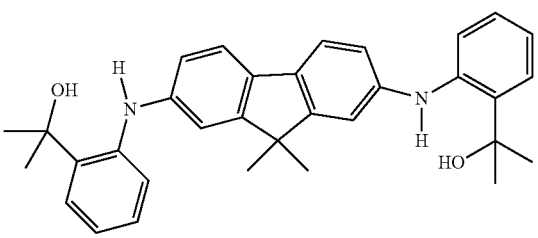 [SMILES: CC(C)(O)c1ccccc1Nc1ccc2c(c1)C(C)(C)c1cc(Nc3ccccc3C(C)(C)O)ccc1-2]

20.0 g (40.60 mmol) of the compound from a) are dissolved in 500 ml of THF, and 147.65 ml (2.2 M solution in diethyl ether) of methyllithium are added dropwise at −78° C. The reaction is subsequently allowed to come slowly to −40° C., and the conversion is monitored by TLC. When the reaction is complete, it is quenched carefully with methanol at −30° C., and the reaction solution is evaporated. Toluene is added to the solid, and the mixture is washed with water. The organic phase is dried over MgSO$_4$ and evaporated in a rotary evaporator, and the residue is recrystallised from ethyl acetate, giving 12.6 g (63%) of the product as a yellowish solid.

c) Bisacridine Compound

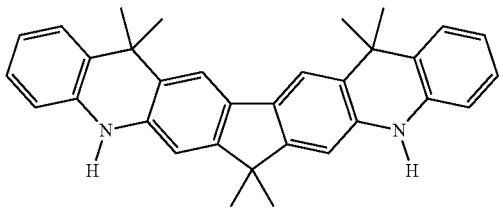 [SMILES: CC1(C)c2ccccc2Nc2cc3c(cc21)-c1cc2c(cc1C3(C)C)Nc1ccccc1C2(C)C]

20.0 g (40.59 mmol) of the compound from b) are initially introduced in 400 ml of toluene, and a mixture of 30 g of polyphosphoric acid and 22 ml of methanesulfonic acid as an emulsion in toluene is added at room temperature. During this addition, the temperature rises to about 40° C., and the mixture is subsequently heated to 50° C. Two phases form, and the product precipitates out as a solid. The toluene phase is separated off, water/ethyl acetate is added to the residue, and the mixture is then carefully adjusted to pH=8 using 20% NaOH solution. The organic phase is separated off and dried over $MgSO_4$, giving 17 g (92%) of the product as a yellow solid.

d) Example Compound 3

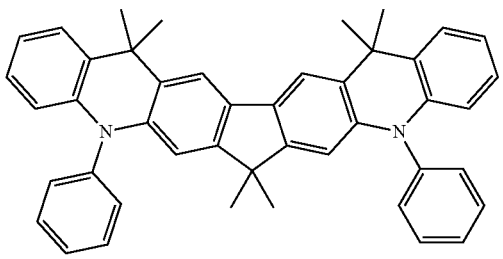 [SMILES: CC1(C)c2cc3c(cc2-c2cc4c(cc21)N(c1ccccc1)c1ccccc1C4(C)C)C(C)(C)c1ccccc1N3c1ccccc1]

100.0 g (219.0 mmol) of the compound from c) are dissolved in 200 ml of toluene, and the solution is degassed. 15.3 ml (1M in toluene) of tris-tert-butylphosphine, 196.67 mg (8.76 mmol) of $Pd(OAc)_2$ and 63.14 g (657.0 mmol) of sodium tert-butoxide are added, and the reaction mixture is heated under reflux for 2.5 h. Water is added to the reaction solution, the phases are separated, the organic phase is dried over $MgSO_4$, and a Soxhlet extraction is carried out over Alox B, giving 65.3 g (81%) of the product as a yellow powder.

Example 4:

Synthesis of Example Compound 4 a) Methyl 2-(4'-bromobiphenyl-4-ylamino)benzoate

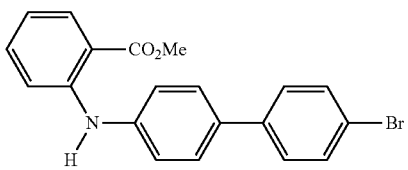 [SMILES: COC(=O)c1ccccc1Nc1ccc(-c2ccc(Br)cc2)cc1]

200 g (641.0 mmol) of 4,4'-dibromobenzene and 41.4 ml (320.5 mmol) of methyl anthranilate are dissolved in 1500 ml of toluene, and the solution is degassed by passing in an inert gas. 229.7 g (705.1 mmol) of $Cs_2CO_3$, 3.59 g (16.02 mmol) of $Pd(OAc)_2$ and 6.29 g (32.05 mmol) of xantphos (4,5-bis(diphenylphosphino)-9,9-dimethylxanthene), all degassed, are subsequently added. The reaction mixture is subsequently stirred at 82° C. for 6 h and filtered through aluminium oxide (basic activity grade 1). The product is purified by column chromatography on silica gel with heptane/toluene (1:49), giving 79.2 g (65%) of the product as a pale-yellow solid.

b) 2-[2-(4'-Bromobiphenyl-4-ylamino)phenyl]propan-2-ol

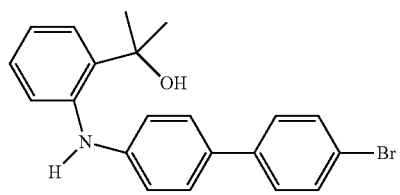 [SMILES: CC(C)(O)c1ccccc1Nc1ccc(-c2ccc(Br)cc2)cc1]

59.7 g (156 mmol) of the compound from a) are initially introduced in 1800 ml of dry THF, and 284.0 ml of a 2M solution of MeLi in $Et_2O$ (624.7 mmol) are added at −78° C., and the mixture is then allowed to warm to −40° C. over the course of 3 h. When the reaction is complete, 300 ml of MeOH are slowly and carefully added at −30° C. in order to quench the excess MeLi. The mixture is allowed to come to room temperature and is concentrated to 1/3, ethyl acetate is added, and the organic phase is washed with water. The organic phase is subsequently dried over $MgSO_4$ and evaporated, giving 59.7 g (quant.) of the product as a solid.

c) 2-(4-Bromophenyl)-9,9-dimethyl-9,10-dihydroacridine

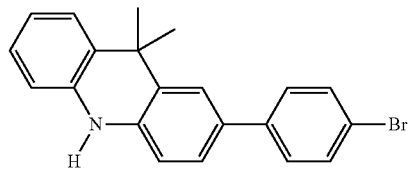

The compound from b) is dissolved in 1000 ml of toluene, and the solution is degassed by passing in an inert gas. A mixture of 178 g of polyphosphoric acid and 123 ml of methanesulfonic acid is added dropwise at RT, and the mixture is heated to 50° C. When the reaction is complete (about 30 min), 20% NaOH solution is carefully added to the reaction solution while cooling well until a pH of 8 has become established. The organic phase is separated off, the water phase is extracted with toluene, and the combined organic phases are subsequently dried over $MgSO_4$ and evaporated, giving 49 g (86%) of the product as a solid.

d) tert-Butyl 2-(4-bromophenyl)-9,9-dimethyl-9H-acridine-10-carboxylate

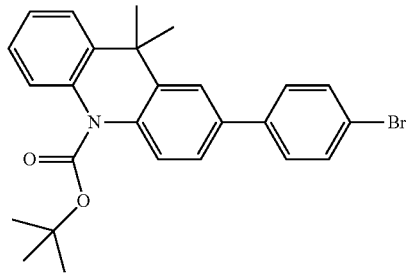 [SMILES: CC(C)(C)OC(=O)N1c2ccccc2C(C)(C)c2cc(-c3ccc(Br)cc3)ccc21]

43.2 ml (188.3 mmol) of di-tert-butyl dicarbonate are dissolved in 600 ml of THF, 49.0 g (134.5 mmol) of the compound from c) are subsequently added, and 1.66 g (13.45 mmol) of DMAP (4-dimethylamino)pyridine are then added. The reaction mixture is heated under reflux for 1.5 h. When the reaction is complete, the reaction solution is carefully added to ice-water, and the organic phase is separated off, washed with water, dried over MgSO$_4$ and evaporated. The yellow oil obtained is taken up in heptane and dissolved at elevated temperature. The product precipitates out as a white precipitate at room temperature, giving 47.7 g (76%) of the product.

e) tert-Butyl 2-[4-(biphenyl-4-ylphenylamino)phenyl]-9,9-dimethyl-9H-acridine-10-carboxylate

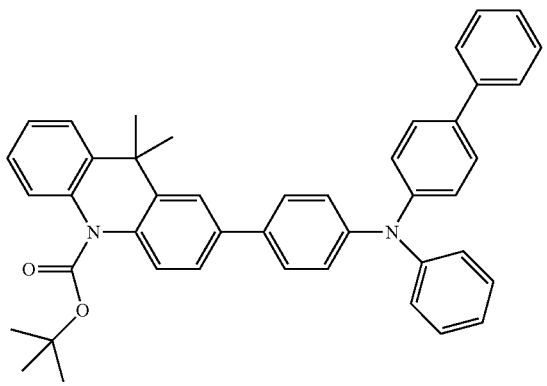 [SMILES: CC(C)(C)OC(=O)N1c2ccccc2C(C)(C)c2cc(-c3ccc(N(c4ccccc4)c4ccc(-c5ccccc5)cc4)cc3)ccc21]

50.0 g (107.7 mmol) of the compound from d) and 34.3 g of biphenyl-phenylamine are dissolved in 500 ml of toluene, and the solution is thoroughly degassed. 2.15 ml (1M in toluene, 2.15 mmol) of tri-tert-butylphosphine, 241.7 mg (1.07 mmol) of PdOAc$_2$ and 15.5 g (161.5 mmol) of sodium tert-butoxide are added. All solids are degassed in advance. The reaction mixture is stirred under reflux and, when the reaction is complete (about 3 h), filtered through aluminium oxide (basic) and purified by column filtration, giving the product as a yellow oil in quantitative yield.

f) Biphenyl-4-yl-[4-(9,9-dimethyl-9,10-dihydroacridin-2-yl)phenyl]-phenylamine

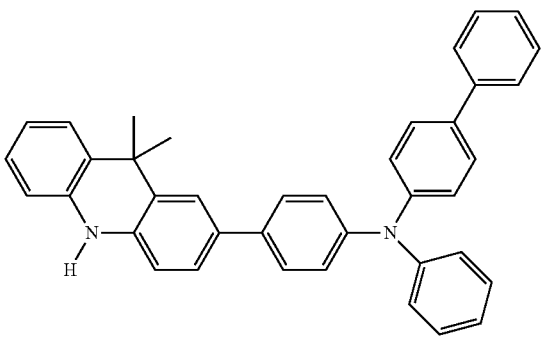 [SMILES: CC1(C)c2ccccc2Nc2ccc(-c3ccc(N(c4ccccc4)c4ccc(-c5ccccc5)cc4)cc3)cc21]

67.7 g (107.7 mmol) of the compound from e) are dissolved in 400 ml of dichloromethane, and 23.9 ml (324 mmol) of trifluoroacetic acid are added at room temperature (RT). The mixture is stirred at RT for 16 h, and the reaction mixture is carefully added to ice-water and then neutralised using 20% NaOH. The mixture is extracted with dichloromethane, dried over MgSO$_4$ and evaporated. After washing by stirring with hot heptane and addition of ethyl acetate at RT, the product (25 g, 68%) precipitates out as a solid.

g) Biphenyl-4-yl-[4-(9,9-dimethyl-10-phenyl-9,10-dihydroacridin-2-yl)-phenyl]phenylamine (Example Compound 4)

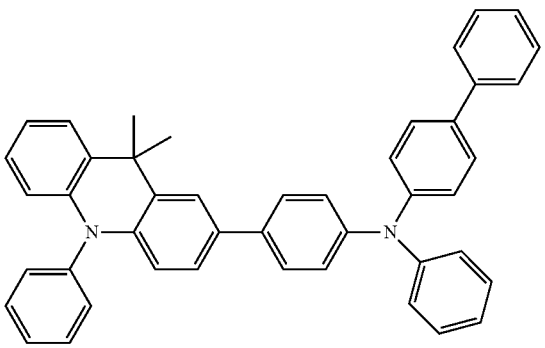 [SMILES: CC1(C)c2ccccc2N(c2ccccc2)c2ccc(-c3ccc(N(c4ccccc4)c4ccc(-c5ccccc5)cc4)cc3)cc21]

38.3 g (72.4 mmol) of the compound from f) and 11.4 ml (108.7 mmol) of bromobenzene are dissolved in 1000 ml of dry toluene, and 5.07 ml (5.07 mmol/1M in toluene) of tri-tert-butylphosphine, 650.6 mg of PdOAc$_2$ and 10.4 g (108.7 mmol) of sodium tert-butoxide are added (the solids are degassed in advance). The reaction mixture is stirred under reflux for 2 h and subsequently filtered through aluminium oxide (basic) while warm. The mixture is subsequently washed by stirring with warm heptane, and sufficient ethyl acetate is added to the warm mixture until an oily solid no longer precipitates out. After cooling to RT, the product precipitates out as a white solid. It is subsequently washed by stirring with hot heptane and ethyl acetate and sublimed, giving 28.7 g (65%) of the product.

Example 5:

Synthesis of Example Compound 5

The synthesis of Example Compound 5 corresponds in the first four steps a) to d) to the synthesis shown in Example 4. The synthetic procedures for the subsequent steps e), f) and g) which give Example Compound 5 are shown below.

e) tent-Butyl 2-[4-(di-o-tolylamino)phenyl]-9,9-dimethyl-9,9a-dihydro-4aH-acridine-10-carboxylate

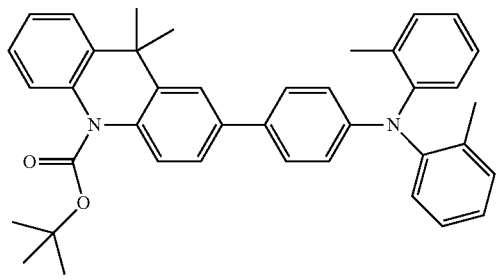 [SMILES: Cc1ccccc1N(c1ccc(-c2ccc3c(c2)C(C)(C)c2ccccc2N3C(=O)OC(C)(C)C)cc1)c1ccccc1C]

35.0 g (75.4 mmol) of the compound from Example 4d) and 19.3 g (97.9 mmol) of di-o-tolylamine are dissolved in 500 ml of dry toluene. 1.5 ml (1.5 mmol/1M in toluene) of tri-tert-butylphosphine, 169.2 mg (0.754 mmol) of Pd(OAc)$_2$ and 10.8 g (113.1 mmol) of NaOtBu are subsequently added (all solids are degassed). The reaction mixture is subsequently stirred under reflux for 2 h and, when the reaction is complete, filtered through Alox B (activity grade 1) and evaporated. The crude product is washed by stirring with hot heptane, giving 23 g (53%) of the product as a solid.

f) [4-(9,9-Dimethyl-9,10-dihydroacridin-2-yl)phenyl]di-o-tolylamine

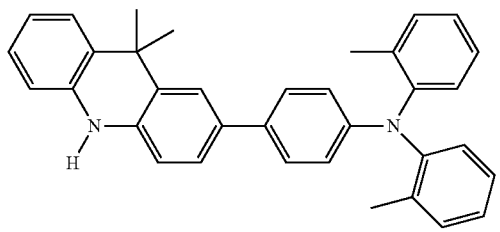 [SMILES: Cc1ccccc1N(c1ccc(-c2ccc3c(c2)C(C)(C)c2ccccc2N3)cc1)c1ccccc1C]

25.1 g (43.2 mmol) of the compound from e) are dissolved in 250 ml of dichloromethane, 9.63 ml (129.7 mmol) of trifluoroacetic acid are subsequently added, and the mixture is stirred at RT for 24 h. The reaction solution is subsequently carefully added to ice-water and neutralised using 20% NaOH with vigorous stirring. The mixture is extracted with dichloromethane, dried and evaporated. The residue in warm toluene is filtered through aluminium oxide (basic) and subsequently washed by stirring with warm heptane, giving 14.3 g (72%) of the product as a white solid.

g) [4-(9,9-Dimethyl-10-p-tolyl-9,10-dihydroacridin-2-yl)phenyl]di-o-tolylamine (Example Compound 5)

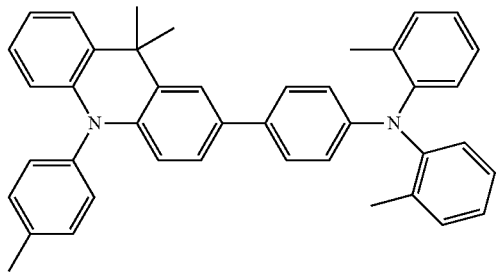 [SMILES: Cc1ccc(N2c3ccccc3C(C)(C)c3cc(-c4ccc(N(c5ccccc5C)c5ccccc5C)cc4)ccc32)cc1]

14.3 g (29.8 mmol) of the compound from f) and 5.4 ml (44.6 mmol) of bromotoluene are dissolved in 100 ml of dry toluene, and the solution is degassed. 2.08 ml (208 mmol) of tri-tert-butylphosphine, 267.1 mg (1.19 mmol) of Pd(OAc)$_2$ and 4.28 g (44.62 mmol) of NaOtBu are added. All solids are thoroughly degassed in advance using argon. The reaction mixture is stirred under reflux for 1 h and, when the reaction is complete, filtered through aluminium oxide (basic). The crude product is crystallised from heptane and ethyl acetate, giving 8.8 g (42%) of the product as a white solid.

Examples 6-11:

Production of OLEDs

OLEDs according to the invention are produced by a general process in accordance with WO 04/058911, which is adapted to the circumstances described here (layer-thickness variation, materials used).

The results for various OLEDs are presented in Examples 6 to 11 below. Glass plates coated with structured ITO (indium tin oxide) form the substrates of the OLEDs. For improved processing, 20 nm of PEDOT (spin-coated from water; purchased from H. C. Starck, Goslar, Germany; poly-(3,4-ethylenedioxy-2,5-thiophene)) are applied to the substrate. The OLEDs consist of the following layer sequence: substrate/PEDOT 20 nm/HIL1 5 nm/hole-transport layer (HTM) 20 or 110 nm/NPB 20 nm/emission layer (EML) 30 nm/Alq$_3$ 20 nm and finally a cathode.

The materials, apart from the PEDOT, are applied by thermal vapour deposition in a vacuum chamber. The emission layer here always consists of a matrix material (host) and a dopant, which is admixed with the host by co-evaporation. The matrix material used in Examples 6 to 11 indicated below is compound H1, which is in each case doped with 10% of D1. These OLEDs exhibit green emission. The cathode is formed by an LiF layer with a thickness of 1 nm and an Al layer with a thickness of 100 nm deposited on top. Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current-voltage-luminance characteristic lines (IUL characteristic lines), and the lifetime are determined. The lifetime is defined as the time after which the initial luminance of 25,000 cd/m$^2$ has dropped to half. The use voltage is defined as the voltage at which the OLED achieves a luminance of 1 cd/m$^2$.

Table 2 shows the results for some OLEDs (Examples 6 to 11). The hole-transport materials according to the invention used are Example Compounds 2 and 3, the synthesis of which has been described above. Compound HTM1 in accordance with the prior art is used as comparison. Example Compounds 2 and 3 are distinguished over compound HTM1 in accordance with the prior art by a lower use voltage and/or a reduced operating voltage and/or significantly improved efficiency, but in particular by improved power efficiency at a luminance of 1000 cd/m$^2$. In addition, use of the compounds according to the invention gives a smaller voltage difference between components having thin (20 nm) and thick (110 nm) HTM layers. This is important in applications, since the optical coupling-out efficiency is optimised crucially by variation of the layer thickness of the hole-transport layer. The lifetimes and colour coordinates of Example Compounds 2 and 3 on use of the compounds according to the invention are very similar or slightly better than on use of compound HTM1 in accordance with the prior art.

An outstanding advantage of the compounds according to the invention is the significantly improved processability compared with the prior art HTM1. Under the same vapour-deposition conditions, the compounds according to the invention exhibit absolutely no tendency to clog the vapour-deposition source, in contrast to the prior art HTM1. The compounds according to the invention are thus significantly more suitable for use in mass production than compound HTM1 in accordance with the prior art. The improved processability of the materials according to the invention is documented for Example Compound 3 in FIG. 1, which shows pictures of the upper edge of the vapour-deposition sources after vapour deposition at a rate of 0.1 nm/s after 1 h and 2 h. As can clearly be seen, the vapour-deposition source is clogged after only 2 h on use of comparative material HTM1 (FIG. 1b)), whereas absolutely no crystallisation at the edge of the vapour-deposition source is evident with Example Compound 3 (FIG. 1d)).

TABLE 1

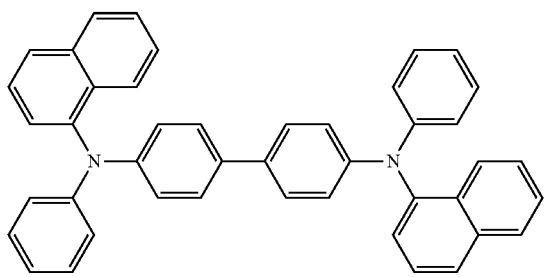 [SMILES: c1ccc(N(c2ccc(-c3ccc(N(c4ccccc4)c4cccc5ccccc45)cc3)cc2)c2cccc3ccccc23)cc1]

NPB

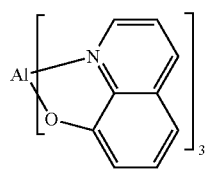

AlQ$_3$

TABLE 1-continued

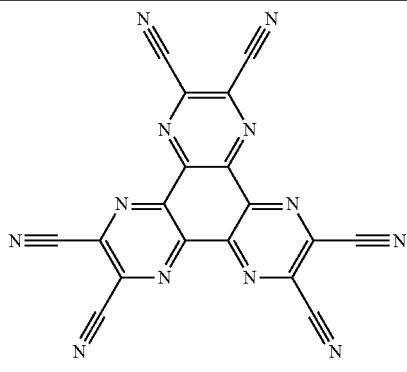

HIL1

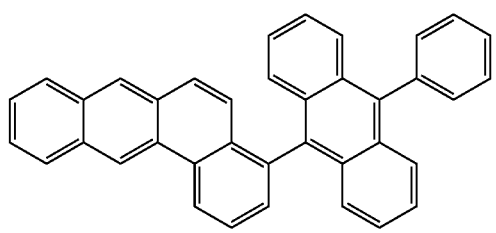 [SMILES: c1ccc(-c2c3ccccc3c(-c3cccc4c3ccc3cc5ccccc5cc34)c3ccccc23)cc1]

H1

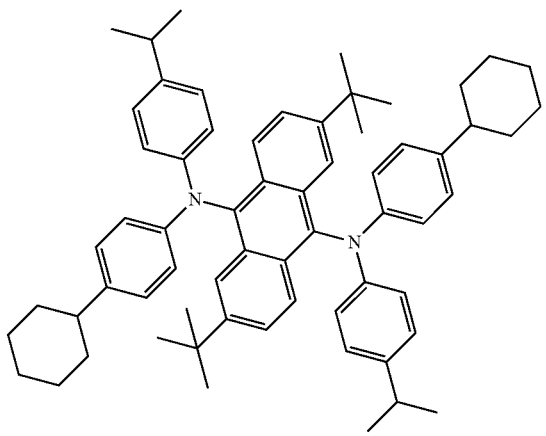 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]

D1

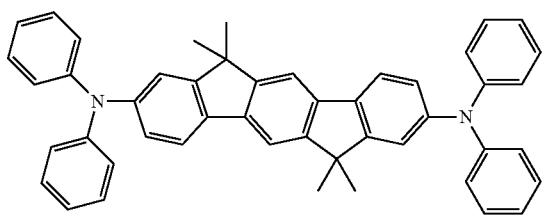 [SMILES: CC1(C)c2cc(N(c3ccccc3)c3ccccc3)ccc2-c2cc3c(cc21)-c1ccc(N(c2ccccc2)c2ccccc2)cc1C3(C)C]

HTM1

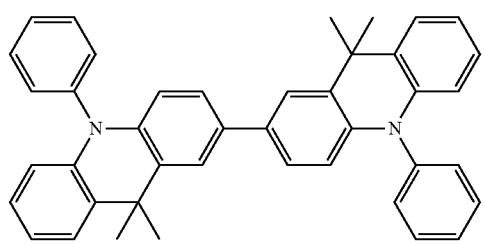 [SMILES: CC1(C)c2ccccc2N(c2ccccc2)c2ccc(-c3ccc4c(c3)C(C)(C)c3ccccc3N4c3ccccc3)cc21]

TABLE 1-continued

Example Compound 2

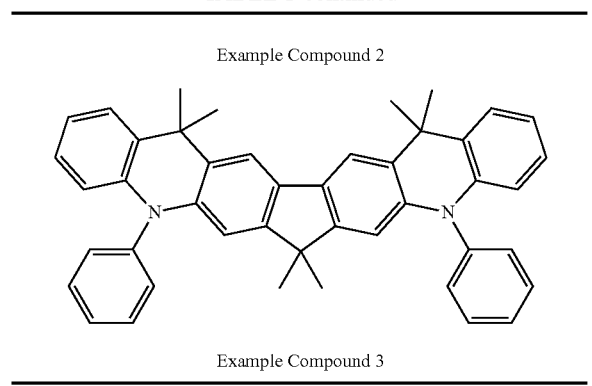

Example Compound 3

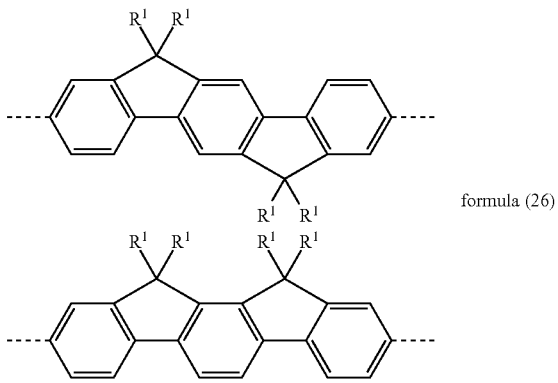  formula (19)

formula (26)

TABLE 2

| Ex. | HTL | Use voltage | Voltage for 1000 cd/m² | Efficiency at 1000 cd/m² | Efficiency at 1000 cd/m² | CIE x/y at 1000 cd/m² | Lifetime for 25000 cd/m² |
|---|---|---|---|---|---|---|---|
| 6 | HTM1 20 nm | 2.8 V | 5.0 V | 17.1 cd/A | 10.7 lm/W | 0.34/0.62 | 355 h |
| 7 | HTM1 110 nm | 3.2 V | 5.5 V | 21.4 cd/A | 12.2 lm/W | 0.31/0.65 | 277 h |
| 8 | Ex. Comp. 2 20 nm | 2.8 V | 4.9 V | 19.8 cd/A | 12.7 lm/W | 0.34/0.63 | 512 h |
| 9 | Ex. Comp. 2 110 nm | 3.1 V | 5.3 V | 22.9 cd/A | 13.6 lm/W | 0.32/0.66 | 485 h |
| 10 | Ex. Comp. 3 20 nm | 2.7 V | 5.0 V | 18.3 cd/A | 11.5 lm/W | 0.33/0.61 | 377 h |
| 11 | Ex. Comp. 3 110 nm | 3.2 V | 5.4 V | 22.1 cd/A | 12.9 lm/W | 0.31/0.64 | 294 h |

The invention claimed is:

1. A compound of the formula (1)

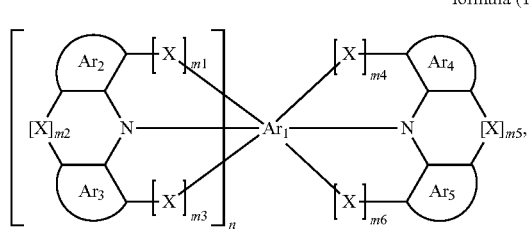

formula (1)

wherein
X is $C(R^1)_2$;
$Ar_1$ is selected from a group of formula (3), (19) or (26)

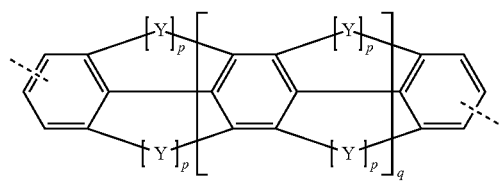

formula (3)

wherein
Y is on each occurrence, identically or differently, a divalent bridge selected from the group consisting of $C(R^1)_2$, $Si(R^1)_2$, O, S, $N(R^1)$, $P(R^1)$;
p is, identically or differently on each occurrence, 0 or 1, where, in the case of p=0, a hydrogen atom or radical $R^1$ is present instead of Y;
q is 0
the symbol "-----" in formula (3) stands for the respective single bond between a C atom of the group of the formula (3) and one of the two nitrogen atoms shown in formula (1); if a group X is bonded to the unit $Ar_1$, this is bonded at the position which is adjacent to the bond to the nitrogen;
the symbol "-----" in the formulae (19) and (26) stands for the respective single bond from $Ar_1$ to one of the nitrogen atoms shown in formula (1);
if a group X is bonded to the unit $Ar_1$, this is bonded at the position which is adjacent to the bond to the nitrogen;
and where the group according to formula (3), (19), and (26) may be substituted by one or more radicals $R^1$;
$Ar_2$ to $Ar_5$ are, identically or differently on each occurrence, an aromatic or heteroaromatic ring system having 5 to 40 aromatic ring atoms, which may in each case be substituted by one or more radicals $R^1$;
$R^1$ is on each occurrence, identically or differently, selected from the group consisting of H, D, F, Cl, Br, I, CHO, $C(=O)Ar_6$, $P(=O)(Ar_6)_2$, $S(=O)Ar_6$, $S(=O)_2Ar_6$, $CR^2=CR^2Ar_6$, CN, $NO_2$, $Si(R^2)_3$, $B(OR^2)_2$, $OSO_2R^2$, a straight-chain alkyl, alkenyl, alkoxy and thioalkoxy group having 1 to 40 C atoms and a branched, mono- or polycyclic alkyl, alkenyl, alkoxy and thioalkoxy group having 3 to 40 C atoms, each of which may be substituted by one or more radicals $R^2$, where one or more non-adjacent $CH_2$ groups may be replaced by $R^2C=CR^2, C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by F, Cl, Br, I, CN or $NO_2$, and an aromatic or hetero-aromatic ring system having 5 to 40 aromatic ring atoms, which may in each case be substituted by one or more radicals $R^2$, and an aryloxy or heteroaryloxy group having 5 to 40 aromatic ring atoms, which may be substituted by one or more radicals $R^2$, and a combination of these systems, where two or more adjacent substituents $R^1$ may also form a mono- or polycyclic, aliphatic or aromatic ring system with one another;

$R^2$ is on each occurrence, identically or differently, selected from the group consisting of H, D, F, Cl, Br, I, CHO, $C(=O)Ar_6$, $P(=O)(Ar_6)_2$, $S(=O)Ar_6$, $S(=O)_2Ar_6$, $CR^3=CR^3Ar_6$, CN, $NO_2$, $Si(R^3)_3$, $B(OR^3)_2$, $OSO_2R^3$, a straight-chain alkyl, alkoxy and thioalkoxy group having 1 to 40 C atoms and a branched, mono- or polycyclic alkyl, alkoxy and thioalkoxy group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $Ge(R^3)_2$, $Sn(R^3)_2$, $CO=O$, $C=S$, $C=Se$, $C=NR^3$, $P(=O)(R^3)$, SO, $SO_2$, $NR^3$, O, S or $CONR^3$ and where one or more H atoms may be replaced by F, Cl, Br, I, CN or $NO_2$, and a combination of these systems, where two or more adjacent substituents $R^2$ may also form a mono- or polycyclic, aliphatic or aromatic ring system with one another;

$R^3$ is on each occurrence, identically or differently, H, F or an aliphatic, aromatic and/or heteroaromatic hydrocarbon radical having 1 to 20 C atoms, in which, in addition, one or more H atoms may be replaced by F atoms, where two or more adjacent substituents $R^3$ may also form a mono- or polycyclic, aliphatic or aromatic ring system with one another;

$Ar_6$ is on each occurrence, identically or differently, an aromatic or hetero-aromatic ring system having 5 to 30 aromatic ring atoms, which may be substituted by one or more radicals $R^3$, where, in addition, two radicals $Ar_6$ which are bonded to the same nitrogen or phosphorus atom may be linked to one another by a single bond or a bridge selected from the group consisting of $B(R^3)$, $C(R^3)_2$, $Si(R^3)_2$, $C=O$, $C=NR^3$, $C=C(R^3)_2$, O, S, $S=O$, $SO_2$, $N(R^3)$, $P(R^3)$ and $P(=O)R^3$;

m1 to m6 are on each occurrence, identically or differently, 0 or 1, where in each case m=0 means that a hydrogen atom or radical $R^1$ is present instead of X, and wherein the indices m1 to m6 are:
m1=m6=1 and m2=m3=m4=m5=0; or
m1=m4=1 and m2=m3=m5=m6=0; or
m1=m2=1 and m3=m4=m5=m6=0; or
m1=1 and m2=m3=m4=m5=m6=0; or
m3=m4=1 and m1=m2=m5=m6=0; and
n is 1.

2. The compound according to claim 1, wherein $Ar_2$, $Ar_3$, $Ar_4$ and $Ar_5$ stand, identically or differently on each occurrence, for phenyl, 1-naphthyl or 2-naphthyl, each of which may be substituted by one or more radicals $R^1$.

3. The compound according to claim 1, wherein of the compound of the formula (1) is a compound of the formula (2)

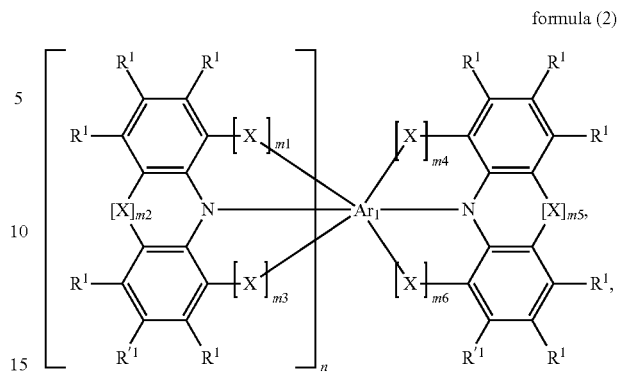

formula (2)

where the symbols and indices used have the meanings indicated in claim 1, and the phenyl groups may furthermore be substituted by one or more radicals $R^1$.

4. The compound according to claim 1, wherein X stands, identically or differently on each occurrence, for a divalent bridge $C(R^1)_2$, where $R^1$ is as defined in claim 1 and is on each occurrence, identically or differently, selected from the group consisting of H, F, a straight-chain alkyl group having 1 to 6 C atoms, where one or more H atoms may be replaced by F, and phenyl and naphthyl, each of which may be substituted by one or more radicals $R^2$, and a combination of these systems, where two or more adjacent substituents $R^1$ may also form a mono- or polycyclic, aliphatic or aromatic ring system with one another.

5. The compound according to claim 1, wherein X stands, identically or differently on each occurrence, for a divalent bridge $C(R^1)_2$, where $R^1$ is as defined in claim 1 and is on each occurrence, identically, selected from the group consisting of H, F, a methyl, where one or more H atoms may be replaced by F, and phenyl which is unsubstituted, and a combination of these systems, where two or more adjacent substituents $R^1$ may also form a mono- or polycyclic, aliphatic or aromatic ring system with one another.

6. The compound according to claim 1, wherein the symbol "-----" stands for the respective single bond between a C atom of the group of the formulae (3) and one of the two nitrogen atoms shown in formula (1); if a group X is bonded to the unit $Ar_1$ it is bonded at the position which is adjacent to the bond to the nitrogen.

7. An oligomer, polymer or dendrimer containing one or more compounds according to claim 1, where one or more bonds to the oligomer, polymer or dendrimer replace one or more bonds to one or more substituents.

8. A process for the preparation of the compound according to claim 1, comprising the following reaction steps:
a) coupling of a substituted group $Ar_1$ to an arylamine which is substituted in the ortho-position, where the aryl group corresponds to the group $Ar_2$ or $Ar_3$ or $Ar_4$ or $Ar_5$; and
b) ring-closure reaction of the substituent in the ortho-position of the arylamine with the group $Ar_1$.

9. An electronic device comprising at least one compound according to claim 1.

10. The electronic device according to claim 9, wherein the device is selected from the group consisting of an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC), an organic laser diode (O-laser) and an organic electroluminescent device (OLED).

11. An organic electroluminescent device which comprises the compound according to claim 1 is employed as hole-transport material in a hole-transport layer and/or in a hole-injection layer.

12. The organic electroluminescent device according to claim 11, wherein the compound is employed as emitting material in an emitting layer.

13. The organic electroluminescent device according to claim 12, wherein the compound is employed as emitting material in an emitting layer, in combination with a host material.

* * * * *